(12) United States Patent
Chokshi et al.

(10) Patent No.: US 12,194,125 B2
(45) Date of Patent: *Jan. 14, 2025

(54) HAIR COSMETIC COMPOSITIONS CONTAINING CATIONIC COMPOUNDS, ACRYLATE-BASED POLYMERS, FATTY COMPOUNDS, AND AMINOFUNCTIONALIZED SILICONES

(71) Applicant: L'OREAL, Paris (FR)

(72) Inventors: Rita Chokshi, Monroe Township, NJ (US); Seyma Aslan, Clifton, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/944,906

(22) Filed: Jul. 31, 2020

(65) Prior Publication Data

US 2022/0031589 A1 Feb. 3, 2022

(51) Int. Cl.
| | |
|---|---|
| *A61Q 5/12* | (2006.01) |
| *A61K 8/34* | (2006.01) |
| *A61K 8/37* | (2006.01) |
| *A61K 8/41* | (2006.01) |
| *A61K 8/73* | (2006.01) |
| *A61K 8/81* | (2006.01) |
| *A61K 8/891* | (2006.01) |
| *A61K 8/97* | (2017.01) |
| *A61Q 5/06* | (2006.01) |

(52) U.S. Cl.
CPC ............. *A61K 8/416* (2013.01); *A61K 8/342* (2013.01); *A61K 8/37* (2013.01); *A61K 8/737* (2013.01); *A61K 8/8147* (2013.01); *A61K 8/8176* (2013.01); *A61K 8/891* (2013.01); *A61K 8/97* (2013.01); *A61Q 5/06* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 2012/0103357 A1* | 5/2012 | Hoffmann | A61K 8/585 132/202 |
| 2018/0092829 A1* | 4/2018 | Comeron | A61K 8/8129 |
| 2018/0311140 A1* | 11/2018 | Perner | A61K 8/44 |

FOREIGN PATENT DOCUMENTS

| | | | | |
|---|---|---|---|---|
| DE | 10001712 A1 | * | 12/2000 | ............... A61K 8/97 |
| DE | 102006059569 A1 | * | 6/2008 | ............... A61K 8/39 |
| WO | WO-2017165931 A1 | * | 10/2017 | ............... A61K 8/37 |

OTHER PUBLICATIONS

DE10001712 Eng Tran. Published: Dec. 21, 2000.*
DE102006059569 Eng Tran. Published: Jun. 19, 2008.*
(Continued)

*Primary Examiner* — Nicole P Babson
*Assistant Examiner* — Lori K Mattison
(74) *Attorney, Agent, or Firm* — POLSINELLI PC

(57) ABSTRACT

The instant disclosure relates to hair cosmetic compositions that include a cationic vinylpyrrolidone copolymer, an acrylate-based polymer, a cationic guar polymer, a cationic surfactant, including a cationizable surfactant, an amino functionalized silicone, a plant-based fatty compound, a fatty alcohol, an ester, and cosmetically acceptable solvent. Methods for using such hair cosmetic compositions are also provided.

15 Claims, 1 Drawing Sheet

(56) References Cited

OTHER PUBLICATIONS

French Search Report and Written Opinion issued Jun. 8, 2021 in French Patent No. 2009019, 7 pages.
Curl Defining Mousse, Mintel GNPD, Record ID 5818749, p. 1-3, Published on Jul. 2018.
Curl Hydration Butter, Mintel GNPD, Record ID 8320357, p. 1-4, Published on Dec. 2020.
Curl Defining Cream, Mintel GNPD, Record ID 8122743, p. 1-3, Published on Sep. 2020.
Final Report on the Safety Assessment of Cetyl Esters, International Journal of Toxicology, 16 (Suppl. 1): pp. 123-130, 1997 Cosmetic Ingredient Review.
International Search Report and Written Opinion issued on Nov. 29, 2021 for corresponding PCT Application No. PCT/US2021/043834.
Database GNPD [Online] MINTEL; Anonymous: "Wave Memoriser," 2014 XP055860247.
Database GNPD [Online] MINTEL; Anonymous: "Switch Curl Cream," 2019 XP055860252.

\* cited by examiner

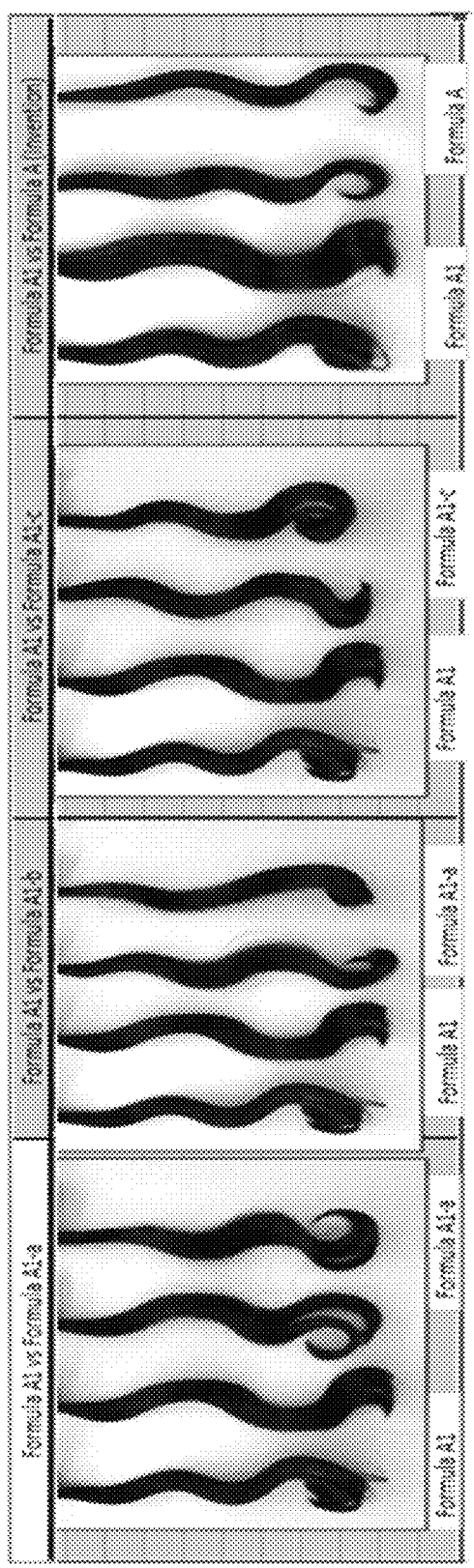

HAIR COSMETIC COMPOSITIONS CONTAINING CATIONIC COMPOUNDS, ACRYLATE-BASED POLYMERS, FATTY COMPOUNDS, AND AMINOFUNCTIONALIZED SILICONES

FIELD OF THE DISCLOSURE

The instant disclosure relates to hair cosmetic compositions that are particularly useful for improving the quality of hair, in particular, curly hair, and which can impart durable styling/shaping attributes to hair. Also disclosed are methods for using the hair cosmetic compositions.

BACKGROUND

Many consumers desire to use cosmetic and care compositions that enhance the appearance of keratinous substrates such as hair, e.g., by changing the color, style, and/or shape of the hair, and/or by imparting various cosmetic properties to hair, such as shine and conditioning. Many of the known compositions and processes for enhancing or preserving the appearance of hair involve chemical treatments to the hair.

The process of changing the color of hair, for example, can involve depositing an artificial color onto the hair which provides a different shade or color to the hair, and/or lifting the color of the hair, such as lightening the color of dark hair to lighter shades, which m requires the use of oxidizing agents.

Additionally, there are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While dyeing or color lifting compositions can effectively alter the color of hair, and relaxing, straightening, perming, and waving compositions can effectively alter the shape of the hair, these chemical treatments can damage the hair fibers and/or irritate the scalp. Thus, in order to reduce or avoid damage to hair, as well as to improve the cosmetic performance of the compositions, different types of hair styling products have been developed by manufacturers that are aimed to help consumers achieve a desired look, including one or more of fuller hair, thicker hair, sleek and straight hair, frizz-free hair, and defined curls. These products are typically provided in forms that are applied after the shampooing and conditioning processes are completed.

Increasingly, consumers also seek hair products that have a natural look and feel, a light-weight feel, while imparting longer-lasting styling or shaping benefits to hair. Further, consumers seek products that offer multiple benefits, for example, combining frizz reduction and style hold with softening, elongation or lengthening effects while still providing good curl definition. Moreover, consumers desire hair products that can protect hair from external factors such as high humidity which causes the hair to become very frizzy, unmanageable, and lose its shape and style or such as mechanical or physical or other external stresses on hair.

One important property sought by consumers of such products is their ability to provide longer lasting style or shape to the hair; for example, a style or shape that lasts over a certain period of time such as overnight or can easily be regained when the consumer wakes up with no or minimal reapplication of the styling product and/or with no or minimal manipulation of the hair to restyle or re-shape the hair and/or with no utilization of mechanical or physical styling devices such as hair rollers, hair pins and clips, head bands, or head caps. Thus, many consumers seek hair products which have excellent style memory as well as long-lasting and/or night care benefits. While different technologies and products exist in the market for hair styling products, there is still a need for improvement in these areas as well as at the same time, the need to provide caring benefits that are not found in a typical or conventional styling product.

Thus, the object of this invention is related to a composition and method of treating hair utilizing hair compositions which will deliver both caring and styling/shaping benefits that are long lasting or durable and can be maintained overnight or when the hair is subjected to changes in the hair shape or style or configuration, and/or to disturbance of the hair fibers and/or to movement of the hair fibers as a result of sleeping or lying down and resting the head on a bed or other surface or the back part of a seat and/or as a result of wearing a head cap or cover. Such styling/shaping benefits are for example, curl definition, as frizz control, discipline, shape control/hold, softness, smoothness, shine, natural feel, hydration, and light weight feel.

The object of the invention is also to deliver all other styling benefits that curly haired consumers desire on a daily basis: curl definition, moisture, conditioning, hold, frizz control, curl/shape retention, curl pick up, moisture to curls, and not leaving the curls feeling greasy or stiff. The composition from such an invention can be applied on wet or damp hair using various techniques such as "wash and go" or "twist out" methods. "Wash and go" involves applying the product, section by section, to wet or damp hair and letting it air dry. The "twist out" method involves manipulating the curl pattern in order to provide elongation while maintaining other styling benefits. It can be done by applying the product on wet hair and twisting small sections of the hair and letting it air dry.

Another object of the invention is deliver the above-described benefits without having to re-apply the product to hair and/or without requiring a lot of time re-styling or re-shaping the hair after a period of time from the first application.

The invention is particularly useful for treating and providing the described properties to hair that is wavy to curly such as hair that is wavy to moderately curly hair.

SUMMARY OF THE DISCLOSURE

It has surprisingly been found that compositions and methods of treating hair according to the present invention impart durable styling/shaping attributes, including curl definition, curl retention, curl pick up, frizz control, volume control, control/hold, discipline, as well as other cosmetic benefits such as fast/easy styling or shaping, hydration, moisture, and smoothness to the hair, while still providing a light weight feel and a clean feel (non-greasy, non-oily) to the hair. These attributes were achieved even after the hair treated with the composition of the invention was subjected to changes in the hair shape or style or configuration, and/or to disturbance of the hair fibers and/or to movement of the hair fibers as a result of sleeping or lying down and resting the head on a bed or other surface or the back part of a seat and/or as a result of wearing a head cap or cover for at least 30 minutes up to several hours such as 8 to 12 hours or overnight (night care benefits).

One aspect of the invention pertains to a hair cosmetic composition comprising:
(a) at least one cationic vinylpyrrolidone copolymer;
(b) at least one acrylate-based polymer;
(c) at least one cationic guar gum;
(d) at least one cationic surfactant, including a cationizable surfactant;
(e) at least one amino functionalized silicone;
(f) at least one plant-based fatty compound;
(g) at least one fatty alcohol;
(h) at least one ester; and
(i) cosmetically acceptable solvent.

Another aspect of the invention pertains to methods of treating hair, such as styling or shaping hair, including imparting durable style or shape to hair. In some embodiments, the method comprises applying any of the compositions described herein to hair. In one or more embodiments, the composition is applied to hair, including curly hair, as part of a hair styling/shaping or caring routine. In some embodiments, the composition is applied after treating the hair with a shampoo and/or conditioner and/or a masque (mask). In some embodiments, the composition is used as a styling/shaping product.

BRIEF DESCRIPTION OF THE DRAWING

Implementation of the present technology will now be described, by way of example only, with reference to the attached figure, wherein:

The FIG. 1 includes pictures of hair swatches treated with the invention and comparative test formulas at time period (T2); i.e., at post-breaking (running the fingers through the hair), after treating the hair and an overnight period of at least 8 hours.

It should be understood that the various aspects are not limited to the arrangements and instrumentality shown in the drawings.

DETAILED DESCRIPTION OF THE DISCLOSURE

The term "hair cosmetic composition" encompasses many types of compositions for application to the hair, for example, hair lotions, hair emulsion creams, hair gel creams, hair conditioners, hair masques (masks), etc., which can be used either as leave-on or rinse-off treatments or products. A hair cosmetic composition according to the invention is characterized by its ability to provide a cosmetic (such as styling/shaping and caring) benefit to the hair. Non-limiting examples of benefits that can be imparted by the compositions of the present invention to hair include long lasting or durable style/shape, as well as one or more of frizz control, curl definition, curl retention, curl pick-up, styling/shaping, discipline, volume control, hold/control, manageability, smoothness, softness, suppleness, hydration (does not feel dry) and natural feel. At the same time, even when the compositions of the present disclosure contain fatty compounds such as fatty alcohols, silicones, and plant- or vegetable-based oils, surprisingly, a light weight feel and a clean feel (non-greasy, non-oily) are imparted to the hair.

The hair cosmetic compositions of the instant disclosure typically include:
(a) at least one cationic vinylpyrrolidone copolymer;
(b) at least one acrylate-based polymer;
(c) at least one cationic guar gum;
(d) at least one cationic surfactant, including a cationizable surfactant;
(e) at least one amino functionalized silicone;
(f) at least one plant-based fatty compound;
(g) at least one fatty alcohol;
(h) at least one ester; and
(i) cosmetically acceptable solvent.

In an embodiment, the at least one cationic vinylpyrrolidone copolymer is selected from copolymers of vinylpyrrolidone and at least one monomer selected from the group consisting of (meth)acrylic acid; (meth)acrylates; unsaturated hydrocarbons; and vinyl monomers.

In an embodiment, the at least one cationic vinylpyrrolidone copolymer is VP/Dimethylaminoethylmethacrylate Copolymer.

In an embodiment, the at least one cationic vinylpyrrolidone copolymer is present in an amount of greater than 0.1 to about 2 wt. %, preferably, about 0.2 to about 1.5 wt. %, more preferably, about 0.3 to about 1 wt. %, or even more preferably, about 0.4 to about 1 wt. %, based on the total weight of the hair cosmetic composition.

In an embodiment, the at least one acrylate-based polymer is selected from acrylates copolymer, polyacrylate-2 crosspolymer, styrene/acrylates copolymer, acrylates/ethylhexyl acrylate copolymer, or mixtures thereof.

In an embodiment, the at least one acrylate-based polymer includes acrylates copolymer.

In an embodiment, the at least one acrylate-based polymer is present in an about 0.05 to about 5 wt %, or about 0.1 to about 4 wt %, or about 0.1 to about 3 wt %, or from about 0.1 to about 2 wt %, or about 0.1 to about 1 wt. %, or about 0.2 to about 0.4 wt. %, based on the total weight of the hair cosmetic composition.

In an embodiment, the at least one cationic guar polymer is selected from guar hydroxypropyltrimonium chloride, hydroxypropyl guar hydroxypropyl trimonium chloride, or a mixture thereof.

In an embodiment, the at least one cationic guar polymer includes guar hydroxypropyltrimonium chloride.

In an embodiment, the at least one cationic guar polymer is guar hydroxypropyltrimonium chloride.

In an embodiment, the at least one cationic guar polymer is present in an amount of about 0.05 to about 1 wt %, or about 0.05 to about 0.8 wt %, or about 0.05 to about 0.7 wt %, or about 0.05 to about 0.6 wt %, or from about 0.1 to about 0.5 wt %, or about 0.2 to about 0.5 wt. %, or about 0.2 to about 0.4 wt. %, based on the total weight of the hair cosmetic composition.

In an embodiment, the at least one cationic surfactant is selected from:
quaternary ammonium salts corresponding to the general formula below:

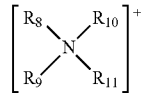

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms;

a quaternary ammonium salt of imidazoline;

a quaternary diammonium or triammonium salt, in particular of formula:

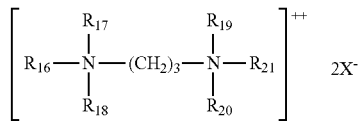

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N$—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates; and cationizable surfactants, including cationizable surfactants together with an acid neutralizer selected from compounds of the general structure $R_4$-$A$-$R_5$—$B$, wherein $R_4$ is a saturated or unsaturated, straight or branched alkyl chain with 8 to 24 C atoms, $R_5$ is a straight or branched alkyl chain with 1 to 4 C atoms, A is selected from:

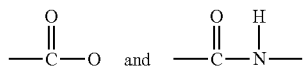

and B is selected from

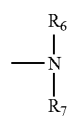

wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms, and

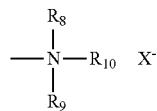

wherein $R_8$ and $R_9$ are the same or different, an alkyl chain with 1 to 4 C atoms, hydroxyl alkyl chain with 1 to 4 C atoms and di hydroxyl alkyl chain with 2 to 4 C atoms, $R_{10}$ is an alkyl chain with 1 to 4 C atoms, hydroxyl alkyl chain with 1 to 4 C atoms or di hydroxyl alkyl chain with 2 to 4 C atoms, or mixtures thereof.

In an embodiment, the at least one cationic surfactant is selected from quaternary diammonium or triammonium salts, in particular of formula:

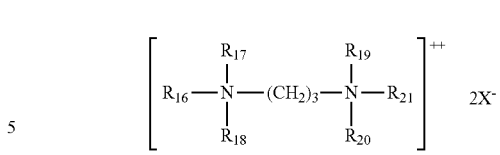

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})$ $(R_{17a})(R_{18a})N$—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates.

In an embodiment, the at least one cationic surfactant is selected from cationizable surfactants, including cationizable surfactants together with an acid neutralizer selected from compounds of the general structure $R_4$-$A$-$R_5$—$B$, wherein $R_4$ is a saturated or unsaturated, straight or branched alkyl chain with 8 to 24 C atoms, $R_5$ is a straight or branched alkyl chain with 1 to 4 C atoms, A is selected from:

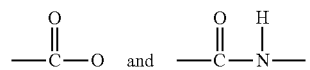

and B is selected from

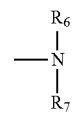

wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms, and

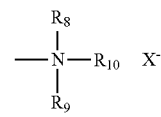

wherein $R_8$ and $R_9$ are the same or different, an alkyl chain with 1 to 4 C atoms, hydroxyl alkyl chain with 1 to 4 C atoms and di hydroxyl alkyl chain with 2 to 4 C atoms, $R_{10}$ is an alkyl chain with 1 to 4 C atoms, hydroxyl alkyl chain with 1 to 4 C atoms or di hydroxyl alkyl chain with 2 to 4 C atoms.

In an embodiment, the at least one cationic surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyl dimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In an embodiment, the at least one cationic surfactant includes behentrimonium chloride.

In an embodiment, the at least one cationic surfactant includes cetrimonium chloride.

In an embodiment, the at least one cationic surfactant is chosen from behentrimonium chloride, cetrimonium chloride, or a mixture thereof.

In an embodiment, the at least one cationic surfactant is selected from oleamidopropyl dimethylamine, linoleamidopropyl dimethylamine, isostearamidopropyl dimethylamine, oleyl hydroxyethyl imidazoline, stearamidopropyl dimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In an embodiment, the at least one cationic surfactant includes stearamidopropyl dimethylamine.

In an embodiment, the at least one cationic surfactant is present in an amount of about 0.2 to about 5 wt. %, preferably, about 0.5 to about 4 wt. %, more preferably, about 0.6 to about 3 wt. %, and even more preferably, about 0.6 to about 2 wt. %, such as from about 0.7 to about 1.5 wt. %, or such as about 0.7 to about 1 wt. %, based on the total weight of the hair cosmetic composition.

In an embodiment, the at least one amino functionalized silicone is selected from amodimethicone, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof.

In an embodiment, the at least one amino functionalized silicone is present in an amount of about 0.1 to about 3 wt. %, or preferably about 0.3 to about 2.5 wt. %, or more preferably, about 0.4 to about 2 wt. %, or about 0.5 to about 1.5 wt. %, based on the total weight of the hair cosmetic composition.

In an embodiment, the at least one plant-based fatty compound is selected from plant-based oils, plant-based butters, plant-based triglycerides, or mixtures thereof.

In an embodiment, the at least one plant-based fatty compound includes shea butter.

In an embodiment, the at least one plant-based fatty compound is present in an amount of about 0.1 to about 10 wt %, about 0.1 to about 9 wt. %, or about 0.2 to about 8 wt. %, or about 0.3 to about 7 wt. %, or about 0.4 to about 7 wt. %, or about 0.4 to about 6.5 wt. %, or about 0.5 to about 6 wt. %, or 0.5 to about 5 wt. %, or about 0.5 to about 4.5 wt. %, or preferably, about 1 to about 4 wt. %, or more preferably, about 1 to about 3 wt. %, or even more preferably, about 1.5 to about 2.5 wt %, based on the total weight of the hair cosmetic composition.

In an embodiment, the at least one fatty alcohol is selected from cetyl alcohol, stearyl alcohol, cetearyl alcohol (combination of cetyl alcohol and stearyl alcohol), behenyl alcohol, lauryl alcohol (1-dodecanol); myristic or myristyl alcohol (1-tetradecanol), arachidyl alcohol (1-eicosanol), lignoceryl alcohol (1-tetracosanol); ceryl alcohol (1-hexacosanol); montanyl alcohol (1-octacosanol); myricylic alcohol (1-triacontanol), decyl alcohol, undecyl alcohol, and a mixture thereof.

In an embodiment, the at least one fatty alcohol is present in an amount of about 1 to about 10 wt. %, or preferably, about 2 to about 9 wt. %, or more preferably, about 3 to about 8 wt. %, or even more preferably, about 3.5 to about 7 wt. %, such as from about 4 to about 7 wt. %, or such from about 4.5 to about 6.5 wt. %, about 5 to about 6 wt. %, based on the total weight of the hair cosmetic composition.

In an embodiment, the composition of the present invention comprises at least one ester selected from fatty esters, cetyl esters, isopropyl esters, glyceryl (glycerol) esters, dialkyl esters, diesters with octanoic acid and propylene glycol (for example, mixture of the propylene glycol diesters of caprylic and capric acids, propylene glycol dicaprylate/dicaprate, or mixtures thereof, preferably, from cetyl esters, isopropyl esters, glyceryl esters, or mixtures thereof.

In an embodiment, the at least one ester is present in an amount of about 0.01 to about 6 wt %, such as about 0.05 to about 5 wt. %, about 0.05 to about 4.5 wt. %, or such as about 0.1 to about 4 wt. %, based on the total weight of the hair cosmetic composition. In an embodiment, the total amount of fatty alcohol(s) is greater than the total amount of ester(s) in the compositions of the present invention, ranges from about 10:1 to about 1:10, including ranges and subranges there between. In an embodiment, the weight ratio of fatty alcohol(s) to ester(s) is greater than 1, or is at about 9:1, 8:1, 7:1, 6;1, 5;1, 4;1, 3:1, 2;1, or 1.5;1.

In an embodiment, the composition of the present invention further comprises at least one nonionic surfactant selected from alkoxylated fatty alcohols, alkylpolyglucosides, polysorbates, or mixtures thereof.

The cosmetically acceptable solvent is selected from water, organic solvents, or a mixture thereof.

In an embodiment, the cosmetically acceptable solvent comprises water.

In an embodiment, the cosmetically acceptable solvent comprises water and at least one organic solvent.

In an embodiment, the hair cosmetic composition of the present invention typically includes:
(a) at least one cationic vinylpyrrolidone copolymer selected from copolymers of vinylpyrrolidone and at least one monomer selected from the group consisting of (meth)acrylic acid; (meth)acrylates; unsaturated hydrocarbons; and vinyl monomers, preferably selected from VP/Dimethylaminoethylmethacrylate Copolymer and present in an amount of about 0.2 to about 1.5 wt. %, or about 0.3 to about 1 wt. %, or about 0.4 to about 1 wt. %;
(b) at least one acrylate-based polymer selected from acrylates copolymer, polyacrylate-2 crosspolymer, styrene/acrylates copolymer, acrylates/ethylhexyl acrylate copolymer, or mixtures thereof, preferably selected from acrylates copolymer and present in an amount of about 0.1 to about 2 wt %, or about 0.1 to about 1 wt. %, or about 0.2 to about 0.4 wt. %;
(c) at least one cationic guar polymer selected from guar hydroxypropyltrimonium chloride, hydroxypropyl guar hydroxypropyl trimonium chloride, or a mixture thereof, preferably selected from guar hydroxypropyltrimonium chloride, and present in an amount of about 0.05 to about 1 wt %, or about 0.1 to about 1 wt. %, or about 0.2 to about 0.5 wt. %;
(d) at least one cationic surfactant, including a cationizable surfactant, selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyl dimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof and present in an amount of preferably, about 0.2 to about 3 wt. %, more preferably, about 0.2 to about 2 wt. %, and even more preferably, about 0.2 to about 1 wt. %;
(e) at least one amino functionalized silicone selected from amodimethicone, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof, preferably selected from amodimethicone and present in an amount of preferably about 0.3 to about 2.5 wt. %, or more preferably, about 0.4 to about 2 wt. %, about 0.5 to about 1.5 wt. %;
(f) at least one plant-based fatty compound selected from plant-based oils, plant-based butters, plant-based triglycerides, or mixtures thereof, preferably, including shea butter, and present in an amount of preferably, about 1 to about 10 wt. %, or more preferably, about 1 to about 8 wt. %, or even more preferably, about 2 to about 6 wt %;
(g) at least one fatty alcohol selected from cetyl alcohol, stearyl alcohol, cetearyl alcohol, or mixtures thereof, and present in an amount of about 4 to about 7 wt. %, or about 4.5 to about 6.5 wt. %, or about 5 to about 6 wt. %;
(h) at least one ester selected from fatty esters, cetyl esters, isopropyl esters, glyceryl (glycerol) esters, dialkyl esters, diesters with octanoic acid and propylene glycol (for example, mixture of the propylene glycol diesters of caprylic and capric acids, INCI: propylene glycol dicaprylate/dicaprate), or mixtures thereof, preferably, from cetyl esters, isopropyl esters, glyceryl esters, or mixtures thereof; and
(i) cosmetically acceptable solvent;
all weights being based on the total weight of the hair cosmetic composition.

In an embodiment, the hair cosmetic composition of the present invention typically includes:
(a) at least one cationic vinylpyrrolidone copolymer selected from VP/Dimethylaminoethylmethacrylate Copolymer and present in an amount of about 0.2 to about 1.5 wt %;
(b) at least one acrylate-based polymer selected from acrylates copolymer, and present in an amount of about 0.1 to about 2 wt %;
(c) at least one cationic guar polymer selected from guar hydroxypropyltrimonium chloride, hydroxypropyl guar hydroxypropyl trimonium chloride, or a mixture thereof, and present in an amount of about 0.05 to about 1 wt %;
(d) at least one cationic surfactant, including a cationizable surfactant, selected from cetrimonium chloride, behentrimonium chloride, behentrimonium methosulfate, stearamidopropyl dimethylamine, and mixtures thereof and present in an amount of about 0.2 to about 3 wt. %;
(e) at least one amino functionalized silicone selected from amodimethicone, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof, and present in an amount of about 0.3 to about 2.5 wt. %;
(f) at least one plant-based fatty compound comprising shea butter, and present in an amount of about 1 to about 6 wt. %;
(g) at least one fatty alcohol selected from cetyl alcohol, stearyl alcohol, cetearyl alcohol, or mixtures thereof, and present in an amount of about 4 to about 7 wt. %, or about 4.5 to about 6.5 wt. %, or about 5 to about 6 wt. %;
(h) at least one ester selected from fatty esters, cetyl esters, isopropyl esters, glyceryl (glycerol) esters, and present in an amount of about 0.1 to about 4 wt. %; and
(i) cosmetically acceptable solvent;
all weights being based on the total weight of the hair cosmetic composition.

In an embodiment, the present invention is further directed to a method of imparting to hair one or more of:
night care benefits;
hydration/moisturization;
shaping or styling hold;
frizz control;
long-lasting frizz control;
manageability;
curl definition;
curl retention;
fast, easy styling/shaping benefits;
long-lasting shape or curl definition;
humidity-resistant curl definition;
volume control;
smoothness;
softness;
natural feel;
conditioning; or
light-weight feel,
the method comprising applying onto hair, any one of the above-described hair cosmetic compositions of the present disclosure.

In an embodiment, the present invention is further directed to a method comprising applying a hair cosmetic composition comprising:
(a) at least one cationic vinylpyrrolidone copolymer;
(b) at least one acrylate-based polymer;
(c) at least one cationic guar gum;

(d) at least one cationic surfactant, including a cationizable surfactant; (e) at least one amino functionalized silicone;
(f) at least one plant-based fatty compound;
(g) at least one fatty alcohol;
(h) at least one ester; and
(i) a cosmetically acceptable solvent.

In an embodiment, the present invention is further directed to a method of preserving or maintaining the style or shape of hair that is exposed to prolonged external influences such as compression and/or deformation and/or humidity, the method comprising applying a hair cosmetic composition comprising:
(a) at least one cationic vinylpyrrolidone copolymer;
(b) at least one acrylate-based polymer;
(c) at least one cationic guar gum;
(d) at least one cationic surfactant, including a cationizable surfactant;
(e) at least one amino functionalized silicone;
(f) at least one plant-based fatty compound;
(g) at least one fatty alcohol;
(h) at least one ester; and
(i) a cosmetically acceptable solvent.

The above compositions, which feature a unique combinations of ingredients, advantageously provide frizz control, volume control, curl definition, curl retention, curl pick-up, discipline, hold/control, styling/shaping, long lasting or humidity-resistant styling and curl care benefits together with natural feel, light-weight feel, non-oily or non-greasy feel, softness, and smoothness.

In certain embodiments, when the hair to be treated and/or styled/shaped is wavy to moderately curly, the cosmetically acceptable solvent in the compositions of the present disclosure preferably include water and propylene glycol. In other embodiments, when the hair to be treated and/or styled/shaped is curlier or has tighter curls, then the cosmetically acceptable solvent in the compositions of the present disclosure preferably include water and glycerin or other higher molecular weight glycol.

The hair cosmetic compositions described herein may be in any suitable physical form. Suitable forms include, but are not limited to low to moderate viscosity liquids, lotions, milks, gel creams, emulsion creams, pastes, clays, conditioners, masks, and the like.

The hair cosmetic compositions may be packaged in a variety of different containers, such as, for example, a ready-to-use container. Non-limiting examples of useful packaging include tubes, jars, caps, unit dose packages, and bottles, including squeezable tubes and bottles and spray bottles.

Cationic Vinylpyrrolidone Copolymer

The at least one cationic vinylpyrrolidone copolymer may be selected from copolymers of vinylpyrrolidone and at least one monomer selected from the group consisting of (meth)acrylic acid; (meth)acrylates; unsaturated hydrocarbons; and vinyl monomers.

In other words, the cationic vinylpyrrolidone copolymer may be obtained by copolymerization of vinylpyrrolidone and at least one co-monomer selected from the group consisting of acrylic acid or methacrylic acid; acrylates or methacrylates; unsaturated hydrocarbons, preferably alkenes such as styrene, butadiene, hexadecene, eicosene, decene, and triacontene; and vinyl monomers.

As examples of the acrylates or methacrylates, mention may be made of methyl acrylate, ethyl acrylates, dimethylaminomethyl acrylate, dimethylaminoethyl acrylate, methyl methacrylate, ethyl methacrylates, dimethylaminoethyl methacrylate, dimethylaminoethyl methacrylate, quaternized dimethylaminomethyl methacrylate, quaternized dimethylaminoethyl methacrylate, and methacrylamidopropyltrimethylammonium.

As examples of the vinyl monomers, mention may be made of vinyl alcohol, vinyl acetate, vinyl propionate, vinyl neodecanoate, vinyl pivalate, vinyl benzoate, vinyl t-butyl benzoate, vinyl caprolactam and methylvinylimidazolium.

The cationic vinylpyrrolidone copolymer may be chosen from the group consisting of: vinylpyrrolidone copolymers comprising dimethylaminoethyl methacrylate units, vinylpyrrolidone copolymers comprising methacrylamidopropyltrimethylammonium units, and vinylpyrrolidone copolymers comprising methylvinylimidazolium units.

The cationic vinylpyrrolidone copolymers comprising dimethylaminoethyl methacrylate units may be chosen from:
vinylpyrrolidone/dimethylaminoethyl methacrylate copolymers; for example, vinylpyrrolidone/dimethylaminoethyl methacrylate copolymer (20/80 by weight) sold under the trade name Copolymer 845 by the company I.S.P., vinylpyrrolidone/dimethylaminoethyl methacrylate copolymers quaternized with diethyl sulphate; for example, vinylpyrrolidone/dimethylaminoethyl methacrylate copolymer quaternized with diethyl sulphate, sold under the trade names Gafquat 734, 755, 755S and 755L by the company I.S.P, vinylpyrrolidone/dimethylaminoethyl methacrylate/hydrophilic polyurethane copolymers; for example, vinylpyrrolidone/dimethylaminoethyl methacrylate/hydrophilic polyurethane copolymer, sold under the trade name Pecogel GC-310 by the company U.C.I. B., or under the trade names Aquamere C 1031 and C 1511 by the company Blagden Chemicals,
vinylpyrrolidone/dimethylaminoethyl methacrylate/C8-C16 olefin copolymers, quaternized or non-quaternized; for example, vinylpyrrolidone/dimethylaminoethyl methacrylate/C8-C16 olefin copolymer sold under the trade names Ganex ACP1050 to 1057, 1062-1069 and 1079-1086 by the company I.S.P.,
and
vinylpyrrolidone/dimethylaminoethyl methacrylate/vinylcaprolactam copolymers; for example, vinylpyrrolidone/dimethylaminoethyl methacrylate/vinylcaprolactam copolymer sold under the trade name Gaffix VC713 by the company I.S.P.

The cationic vinylpyrrolidone copolymers comprising methacrylamidopropyltrimethylammonium (MAPTAC) units may be chosen from: vinylpyiTolidone/methaciylamidopropyltrimethylammonium copolymers; for example, vinylpyrrolidone/MAPTAC copolymer sold under the trade names Gafquat ACP1011 and Gafquat HS100 by the company I.S.P.,
and
vinylpyrrolidone/methaciylamidopropyltrimethylammonium/vinylcaprolactam terpolymers; for example, vinylpyrrolidone/MAPTAC/vinylcaprolactam terpolymer sold under the trade names Polymer ACP 1059, 1060 and 1156 by the company I.S.P. The cationic vinylpyrrolidone copolymers comprising methylvinylimidazolium units may be chosen from vinylpyrrolidone/methylvinylimidazolium chloride copolymers; for example, vinylpyrrolidone/methylvinylimidazolium chloride copolymer sold under the trade names Luviquat FC370, FC550, FC905 and HM552 by the company BASF, vinylpyrrolidone/methylvinylimidazolium chloride/vinylimidazole copolymers; for example, vinylpyrrolidone/methylvinylimidazolium chloride/vinylimidazole copolymer sold under the trade name Luviquat 8155 by the company BASF, vinylpyrrolidone/vinyl caprolactam/vinylimidazolium copolymers; for example, vinylpyrrolidone/vinylcaprolactam/vinylimidazolium methosulfate copolymer sold under the trade name Luviquat Hold by the company BASF, and vinylpyrrolidone/methylvinylimidazolium methosulphate copolymers; for example, vinylpyrrolidone/methylvinylimidazolium methosulphate copolymer sold under the trade name Luviquat MS370 by the company BASF.

It may be preferable that the cationic vinylpyrrolidone copolymer be chosen from vinylpyrrolidone polymers comprising dimethylaminoethyl methacrylate units, more preferably chosen from vinylpyrrolidone/dimethylaminoethyl methacrylate copolymers, for example those sold under the name COPOLYMER 845-0 by the company ISP ASHLAND.

It may be preferable that the cationic vinylpyrrolidone copolymer be chosen from vinylpyrrolidone polymers comprising methacrylamidopropyltrimethylammonium units, and more preferably Polyquaternium-28.

It may also be preferable that the cationic vinylpyrrolidone copolymer be chosen from vinylpyrrolidone polymers comprising methylvinylimidazolium units, more preferably chosen from vinylpyrrolidone/methylvinylimidazolium copolymers, and even more preferably Polyquaternium-16 for example those sold under the trade name LUVIQUAT FC 370 by the company AROMAT.

The total amount of the cationic vinylpyrrolidone copolymer in the composition, if present, may vary but is typically from greater than 0.1 to about 2 wt. %, based on the total weight of the composition. In some instances, the total amount of cationic vinylpyrrolidone copolymer is in an amount of about 0.1 to about 2 wt. %, or about 0.2 to about 1.9 wt. %, or about 0.3 to about 1.8 wt. %, or about 0.4 to about 1.7 wt. %, or about 0.5 to about 1.6 wt. %, or about 0.6 to about 1.5 wt. %, or about 0.7 to about 1.4 wt. %, or about 0.7 to about 1.3 wt. %, or about 0.7 to about 1.2 wt. %, about 0.7 to about 1.1 wt. %, or about 0.7 to about 1 wt. %, or about 0.7 to about 0.9 wt. %, based on the total weight of the composition, including ranges and sub-ranges there between.

Thus, the cationic vinylpyrrolidone copolymer is present, by weight, based on the total weight of the composition, in an amount from about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, to about 2 wt. %, including increments and ranges therein and there between.

Acrylate-Based Polymer

The acrylate-based polymer of the compositions of the present invention may selected from acrylate latex polymers or acrylate non-latex polymers. The acrylate-based polymer of the compositions of the present invention may be anionic or nonionic polymers. Preferably, the acrylate-based polymer of the compositions of the present invention is selected from nonionic acrylate-based latex or non-latex polymers.

Acrylate latex polymers may be chosen from acrylate latex polymers, such as those resulting from the homopolymerization or copolymerization of monomers chosen from (meth)acrylics, (meth)acrylates, (meth)acrylamides and/or vinyl homopolymers or copolymers. The term "(meth)acryl" and variations thereof, as used herein, means acryl or methacryl.

In certain embodiments, the (meth)acrylic monomers may be chosen from acrylic acid, methacrylic acid, citraconic acid, itaconic acid, maleic acid, fumaric acid, crotonic acid, maleic anhydride, or mixtures thereof.

In certain embodiments, the (meth)acrylic monomers may be chosen from C1-C8 alkyl (meth)acrylic, methyl (meth)acrylic, ethyl (meth)acrylic, propyl (meth)acrylic, isopropyl (meth)acrylic, butyl (meth)acrylic, tert-butyl (meth)acrylic, pentyl(meth) acrylic, isopentyl (meth)acrylic, neopentyl (meth)acrylic, hexyl (meth)acrylic, isohexyl (meth)acrylic, 2-ethylhexyl (meth)acrylic, cyclohexyl (meth)acrylic, isohexyl (meth)acrylic, heptyl (meth)acrylic, isoheptyl (meth)acrylic, octyl (meth)acrylic, isooctyl (meth)acrylic, or mixtures thereof.

In certain embodiments, the esters of (meth)acrylic monomers may be chosen from C1-C8 alkyl (meth)acrylate, methyl (meth)acrylate, ethyl (meth)acrylate, propyl (meth)acrylate, isopropyl (meth)acrylate, butyl (meth)acrylate, tert-butyl (meth)acrylate, pentyl(meth) acrylate, isopentyl (meth)acrylate, neopentyl (meth)acrylate, hexyl (meth)acrylate, isohexyl (meth)acrylate, 2-ethylhexyl (meth)acrylate, cyclohexyl (meth)acrylate, isohexyl (meth)acrylate, heptyl (meth)acrylate, isoheptyl (meth)acrylate, octyl (meth)acrylate, isooctyl (meth)acrylate, allyl (meth)acrylate, or combinations thereof.

In certain embodiments, the esters of (meth)acrylic monomers may be chosen from C1-C8 alkoxy (meth)acrylate, methoxy (meth)acrylate, ethoxy (meth)acrylate, propyl oxide (meth)acrylate, isopropyl oxide (meth)acrylate, butyl oxide (meth)acrylate, tert-butyl oxide (meth)acrylate, pentyl oxide (meth) acrylate, isopentyl oxide (meth)acrylate, neopentyl oxide (meth)acrylate, C2-C6 hydroxy alkyl (meth) acrylates, hydroxy ethyl (meth)acrylate, 2-hydroxypropyl (meth)acrylate, glycidyl (meth)acrylate, ethylene glycol di(meth)acrylate, polyethylene glycol mono(meth)acrylate, 1,4-butane diol di(meth)acrylate, 1,6, hexane diol di(meth)acrylate, aryl (meth)acrylates benzyl (meth)acrylate, phenyl (meth)acrylate, or mixtures thereof.

In certain embodiments, the esters can further contain amino groups such as aminoethyl (meth)acrylate, N,N-dimethylaminoethyl (meth)acrylate, N,N-dimethylaminopropyl (meth)acrylate, N,N-dimethylaminodimethylpropyl (meth)acrylate, N,N-diethyleaminoethyl (meth)acrylate, N,N,N-trimethylaminoethyl (meth)acrylate, salts of the ethylenic amines, or silicone macromonomers.

In various embodiments, the alkyl group of the esters may be either fluorinated or perfluorinated, for example one, some, or all of the hydrogen atoms of the alkyl group are substituted with fluorine atoms. In other embodiments, the monomers can also be fluorine-containing monomers, such as trifluoroethyl methacrylate, 2,2,3,3-tetrafluoropropyl methacrylate, 2,2,3,3,4,4-hexafluorobutyl methacrylate, perfluorooctyl methacrylate, or perfluorooctyl acrylate.

In certain embodiments, the amides of (meth)acrylic monomers can, for example, be made of (meth)acrylamide, N-alkyl (meth)acrylamides, N—(C1-C12) alkyl (meth)acrylates such as N-ethyl (meth)acrylamide, N-t-butyl (meth)acrylamide, N-t-octyl (meth)acrylamide, N-methylol (meth)acrylamide, N-diacetone (meth)acrylamide, or mixtures thereof.

In certain embodiments, the vinyl monomers can include, but are not limited to, vinyl cyanide compounds such as acrylonitrile or methacrylonitrile; vinyl esters such as vinyl formate, vinyl acetate, vinyl propionate, vinyl neodecanoate, vinyl pivalate, vinyl benzoate, vinyl t-butyl benzoate, or triallyl cyanurate; vinyl halides such as vinyl chloride or vinylidene chloride; aromatic mono- or divinyl compounds such as styrene, a-methylstyrene, chlorostyrene, alkylstyrene, divinylbenzene or diallyl phthalate; or mixtures thereof. In other embodiments, the vinyl monomers can include para-styrensulfonic, vinylsulfonic, 2-(meth)acryloyloxyethylsulfonic, or 2-(meth)acrylamido-2-methylpropylsulfonic acids.

The list of monomers given is not limiting, and it should be understood that it is possible to use any monomer known to those skilled in the art which includes acrylic and/or vinyl monomers (including monomers modified with a silicone chain).

In certain embodiments, silicone acrylic polymers may also optionally be used as vinyl polymer in at least one exemplary and non-limiting embodiment.

In certain embodiments, the acrylate latex polymer may be chosen from, for example, an ammonium acrylates copolymer, an acrylates copolymer, a (meth)acrylate copolymer, a butyl acrylate/hydroxypropyl dimethicone acrylate copolymer, an acrylates/$C_{12}$-$C_{22}$ alkylmethacrylate copolymer, an acrylates copolymer in combination with isododecane, an acrylates/octylacrylamide copolymer, and combinations thereof.

In some instances, the acrylate latex polymer is acrylates copolymer.

In certain embodiments, acrylic latex polymers may be chosen from aqueous dispersions of Methacrylic Acid/Ethyl Acrylate copolymer (INCI name: Acrylates Copolymer, such as LUVIFLEX Soft sold by the company BASF), PEG/PPG-23/6 Dimethicone Citraconate/C10-30 Alkyl PEG-25 Methacrylate/Acrylic Acid/Methacrylic Acid/Ethyl Acrylate/Trimethylolpropane PEG-15 Triacrylate copolymer (INCI name: Polyacrylate-2 Crosspolymer, such as FIXATE Superhold sold by the company Lubrizol), Butyl acrylate, PEG-10 acrylate, PPG-6 acrylate and dimethylacrylamide copolymer (INCI name: Polyacrylate-3 crosspolymer), Styrene/Acrylic copolymer (such as NEOCRYL A-1120 sold by the company DSM), Ethylhexyl Acrylate/Methyl Methacrylate/Butyl Acrylate/Acrylic Acid/Methacrylic Acid copolymer (INCI name: Acrylates/Ethylhexyl Acrylate Copolymer, such as DAITOSOL 5000SJ sold by the company Daito Kasei Kogyo), Acrylic/Acrylates Copolymer (INCI name: Acrylates Copolymer, such as DAITOSOL 5000AD sold by the company Daito Kasei Kogyo), or Acrylic copolymers and Acrylates Copolymers (such as VINYSOL 2140 sold by the company Daido Chemical, ACULYN 33 sold by the company Dow Chemical, LUVIMER MAE sold by the company BASF, or BALANCE CR sold by the company Akzo Nobel).

In an embodiment, the acrylate non-latex polymer is chosen from polyacrylate-3, commercially known under the trade name of VISCOPHOBE DB-100 and sold by The Dow Chemical Company, carbomers, commercially known under the trade name of CARBOPOL polymers and sold by Lubrizol Advance Materials, Inc., acrylates/C10-30 alkyl acrylate crosspolymers, commercially known the trade names of PEMULEN TR-1 and PEMULEN TR-2 polymers, and sold by Lubrizol Advance Materials, Inc, Acrylates/C10-30 Alkyl Acrylate Crosspolymer such as CARBOPOL ULTREZ 20 Polymer by and sold by Lubrizol Advance Materials, Inc., AMP-acrylates/allyl methacrylate copolymer, commercially known under the trade name of FIXATE G-100 polymer and sold by Lubrizol Advance Materials, Inc., Polyacrylate Crosspolymer-6 such as SEPIMAX Zen by the company Seppic, and a crosslinked methacrylic acid/ethyl acrylate copolymer, also known as an acrylates copolymer in aqueous dispersion, such as the slightly crosslinked, alkali-swellable acrylate polymer known by the INCI name acrylates copolymer and sold by Lubrizol, under the tradename CARBOPOL AQUA SF-1 as an aqueous dispersion.

The total amount of the acrylate-based polymer in the composition, if present, may vary but is typically from greater than 0.01 to about 5 wt. %, based on the total weight of the composition. In some instances, the total amount of acrylate-based polymer is in an amount of about 0.05 to about 5 wt %, or about 0.1 to about 4 wt %, or about 0.1 to about 3 wt %, or from about 0.1 to about 2 wt %, or about 0.1 to about 1 wt. %, or about 0.15 to about 0.6 wt. %, or about 0.2 to about 0.4 wt. %, based on the total weight of the composition, including ranges and sub-ranges there between.

Thus, the acrylate-based polymer is present, by weight, based on the total weight of the composition, in an amount from about 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, to about 2 wt. %, including increments and ranges therein and there between.

Cationic Guar Polymer

The cationic guar polymer in the composition may be selected from guar hydroxypropyltrimonium chloride, hydroxypropyl guar hydroxypropyl trimonium chloride, or a mixture thereof.

In an embodiment, the at least one cationic guar polymer includes guar hydroxypropyltrimonium chloride.

In an embodiment, the at least one cationic guar polymer is guar hydroxypropyltrimonium chloride.

The total amount of the cationic thickening agent in the composition may vary but is typically present in an amount of about 0.05 to about 1 wt %, or about 0.05 to about 0.8 wt %, or about 0.05 to about 0.7 wt %, or about 0.05 to about 0.6 wt %, or from about 0.1 to about 0.5 wt %, or about 0.2 to about 0.5 wt. %, or about 0.2 to about 0.4 wt. %, based on the total weight of the hair cosmetic composition.

Thus, the cationic guar polymer is present, by weight, based on the total weight of the composition, in an amount from about 0.05, 0.075, 0.1, 0.125, 0.15, 0.175, 0.2, 0.225, 0.25, 0.275, 0.3, 0.325, 0.35, 0.375, 0.4, 0.425, 0.45, 0.475, 0.5 to about 1 wt. %, including increments and ranges therein and there between.

Cationic Surfactants Including Cationizable Surfactants

In accordance with the disclosure, compositions hereof may include at least one cationic surfactant. The term "cationic surfactant" means a surfactant that may be positively charged when it is contained in the compositions according to the disclosure. This surfactant may bear one or more positive permanent charges or may contain one or more functional groups that are cationizable in the composition according to the disclosure. Non-limiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyl dimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In some embodiments, the cationic surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyl dimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

In some embodiments, the cationic surfactant comprises cetrimonium chloride, behentrimonium chloride, and mixtures thereof. Behentrimonium Chloride, also described by the technical names that include 1-Docosanaminium, N,N,N-Trimethyl-, Chloride, and N,N,N-Trimethyl-1-Docosanaminium Chloride, is the quaternary ammonium salt that conforms to the formula:

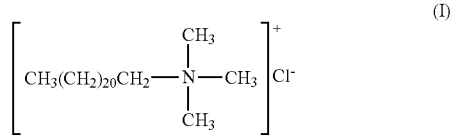

(I)

In accordance with some embodiments, the amount of each of the at least one cationic surfactant is from about 0.1 to about 5 wt. %, preferably, about 0.2 to about 3 wt. %, and more preferably, about 0.2 to about 2 wt. %, and even more preferably, about 0.2 to about 1 wt. %, or any suitable combination, sub-combination, range, or sub-range thereof by weight, based on the weight of the composition. One of ordinary skill in the art, however, will appreciate that other ranges are within the scope of the invention. In some particular embodiments, the at least one cationic surfactant, including cationizable surfactants together with an acid neutralizer, is present from about 0.1 to about 5 wt. %, and an acid neutralizer is present from about 0.0.5 to about 1 wt. %, based on the weight of the composition.

Thus, any one of the at least one cationic surfactant is present, by weight, based on the total weight of the composition, from about 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.4, 2.5, 2.6, 2.7, 2.8, 2.9, 3, 3.2, 3.4, 3.5, 3.6, 3.8, 4, 4.2, 4.4, 4.5, 4.6, 4.8, to about 5 wt. %, including increments and ranges therein and there between.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The cationic surfactant(s) may also be chosen from optionally polyoxyalkylenated, primary, secondary or tertiary fatty amines, or salts thereof, and quaternary ammonium salts, and mixtures thereof.

In some cases, it is useful to use salts such as chloride salts of the quaternary ammonium compounds.

The fatty amines generally comprise at least one $C_8$-$C_{30}$ hydrocarbon-based chain.

A. Examples of quaternary ammonium salts that may especially be mentioned include: those corresponding to the general formula below:

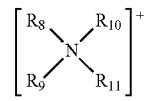

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and, in some embodiments, from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

B. a quaternary ammonium salt of imidazoline, such as, for example, those of formula below:

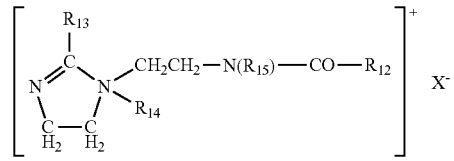

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylaryl-sulfonates in which the alkyl and aryl groups, in some embodiments, comprise, respectively, from 1 to 20 carbon atoms and from 6 to 30 carbon atoms. $R_{12}$ and $R_{13}$, in some embodiments, denote a mixture of alkenyl or alkyl groups containing from 12 to 21 carbon atoms, derived for example from tallow fatty acids, $R_{14}$, in some embodiments, denotes a methyl group, and $R_{15}$, in some embodiments, denotes a hydrogen atom. Such a product is sold, for example, under the name REWOQUAT W 75 by the company Rewo;

C. a quaternary diammonium or triammonium salt, in particular of formula:

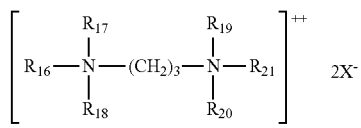

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N$—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), D. Cationic/cationizable surfactants, including cationizable surfactants together with an acid neutralizer, for example of the general structure R4-A-R5-B wherein R4 is a saturated or unsaturated, straight or branched alkyl chain with 8 to 24 C atoms, R5 is a straight or branched alkyl chain with 1 to 4 C atoms, A is selected from:

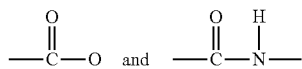

and B is selected from

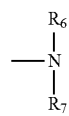

wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms, and

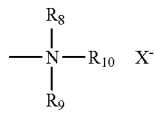

wherein $R_8$ and $R_9$ are the same or different, an alkyl chain with 1 to 4 C atoms, hydroxyl alkyl chain with 1 to 4 C atoms and di hydroxyl alkyl chain with 2 to 4 C atoms, R.sub.10 is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24C atoms, in some embodiments, 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, steara midopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants or amphiphilic surfactants may be chosen from fatty alkylamines. in some embodiments, fatty dialkylamines. In some cases, the fatty dialkylamines may be fatty dimethylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, oleyl hydroxyethyl imidazoline, stearamidopropyl dimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamido-ethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereof are useful, especially in combination with fatty dimethylamines such as, for example, stearamidopropyl dimethylamine.

Amino Functionalized Silicones

The silicones may be hydrophobic or, in some instances, be functionalized to be hydrophilic. Preferably, the silicones of the hair treatment compositions are amino functionalized silicone. The term "amino-functionalized silicone" means a silicone containing at least one primary amino, secondary amino, tertiary amino and/or quaternary ammonium group. The structure of the amino-functionalized silicone may be linear or branched, cyclic or non-cyclic. The amino functional group may be at any position in the silicone molecule, preferably at the end of the backbone (for example, in the case of amodimethicones) and/or in the side chain.

In some instances, the amino-functionalized silicones are selected from compounds of the following formula:

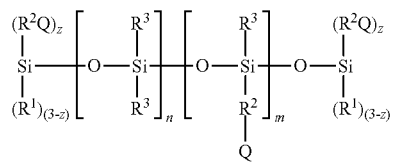

wherein each $R^1$ is independently selected from a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group (preferably, each $R^1$ is independently selected from a $C_{1-30}$ alkyl group, a $C_{1-30}$ alkoxy group and a hydroxy group);

each $R^2$ is independently a divalent alkylene radical having one to ten carbon atoms (preferably, $R^2$ is a divalent alkylene radical having three to six carbon atoms);

each $R^3$ is independently selected from a $C_{1-30}$ alkyl group, a $C_{5-30}$ aryl group, a $C_{6-30}$ aralkyl group and a $C_{1-30}$ alkaryl group (preferably, each $R^3$ is independently selected from of a $C_{1-30}$ alkyl group);

Q is a monovalent radical selected from —$NR^4_2$ and —$NR^4(CH_2)_xNR^4_2$;

each $R^4$ is independently selected from a hydrogen and a $C_{1-4}$ alkyl group;

x is 2 to 6;

z is 0 or 1;

n is 25 to 3,000 (preferably, 25 to 2,000; more preferably, 25 to 1,000; most preferably 25 to 500); and m is 0 to 3,000 (preferably, 0 to 2,000; more preferably, 0 to 1,000; most preferably, 0 to 100);

with the proviso that at least 50 mol % of the total number of $R^1$ and $R^3$ groups are methyl and with the proviso that when m is 0, z is 1.

Preferred $R^1$ groups include methyl, methoxy, ethyl, ethoxy, propyl, propoxy, isopropyl, isopropoxy, butyl, butoxy, isobutyl, isobutoxy, phenyl, xenyl, benzyl, phenylethyl, tolyl and hydoxy. Preferred $R^2$ divalent alkylene radicals include trimethylene, tetramethylene, pentamethylene, —$CH_2CH(CH_3)CH_2$— and —$CH_2CH_2CH(CH_3)CH_2$—. Preferred $R^3$ groups include methyl, ethyl, propyl, isopropyl, butyl, isobutyl, phenyl, xenyl, benzyl, phenylethyl and tolyl. Preferred $R^4$ groups include methyl, ethyl, propyl, isopropyl, butyl and isobutyl. When z is 0, the amino-functionalized silicone has only pendant amine functional substituents in the polymer chain. When z is 1, the amino-functional silicone may have only terminal amine functional substituents (e.g., m=0) or may have both terminal and pendant amine functional substituents in the polymer chain (e.g., m>0). Preferably, n+m is 50 to 1,000. More preferably, n+m is 50 to 750. Still more preferably, n+m is 50 to 500. Most preferably, n+m is 50 to 250.

In some instances, the amino-functionalized silicones are alkoxylated and/or hydroxylated amino silicones. Suitable alkoxylated and/or hydroxylated amino silicones may be selected from compounds having a structure in accordance with the following formula:

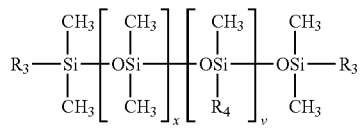

wherein $R_3$ is hydroxyl or $OR_5$, $R_5$ is a $C_1$ to $C_4$ alkyl group, $R_4$ is a group with a structure according to the following formula:

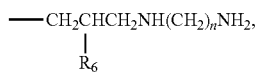

wherein $R_6$ is a $C_1$ to $C_4$ alkyl, n is a 1 to 4, x is the same as "n" described above, and y is the same as "m" described above.

Non-limiting examples of amino-functionalized silicones include bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. In some instances, a particularly useful amino-functionalized silicone is bis-hydroxy/methoxy amodimethicone, wherein X is isobutyl and one of the R is OH and the other is $OCH_3$ in the above structure, also known as "Bis-Hydroxy/Methoxy Amodimethicone" and "3-[(2-aminoethyl)amino]-2-methylpropyl Me, di-Me, [(hydroxydimethylsilyl)oxy]- and [(methoxydimethylsilyl)oxy]-terminated." Bis-hydroxy/methoxy amodimethicone is commercially available under the tradename DOWSIL AP-8087 FLUID from The Dow Chemical Company.

The silicone of the hair treatment composition may, in some instances, include polydiorganosiloxanes, e.g., polydimethylsiloxanes having the CTFA designation dimethicone. Additional silicones that may be suitable for the hair treatment compositions include (particularly for shampoos and conditioners) polydimethyl siloxanes having hydroxyl end groups, which have the CTFA designation dimethiconol. Silicone gums may, in some instances, be included in the hair treatment compositions, such as those having a slight degree of cross-linking. Non-limiting examples of silicone gums that may, optionally, be included are described in WO 96/31188, which is incorporated herein by reference for all purposes.

The silicone(s) may have a viscosity of at least 10,000 cst, such as at least 50,000 cst, at least 100,000 cst, at least 200,000 cst, at least 400,000 cst, at least 800,000 cst, at least 1,000,000 cst, or at least 2,000,000 cst. Preferably the viscosity does not exceed $10^9$ cst for ease of formulation.

The hair treatment composition may include pre-formed emulsions of silicones, such as emulsions XIAMETER 2-8299 (Dow Corning/Dow Chemical), BELSIL ADM 4000 E (Wacker), DC2-1766, DC2-1784, and microemulsions DC2-1865 and DC2-1870 from Dow Corning, or cross-linked silicone gums, such as DC X2-1787 or DC X2-1391 from Dow Corning.

In an embodiment, the amino functionalized silicone of the compositions of the present invention includes amodimethicone. The amodimethicone may be commercially available as an emulsion comprising amodimethicone, trideceth-6, and cetrimonium chloride under the tradenames XIAMETER 2-8299 or DOWSIL 2-8299 (Dow Corning/Dow Chemical). The amodimethicone may also be available as an emulsion under the tradename, BELSIL ADM 4000 E (Wacker).

In accordance with the various embodiments, the amount of the at least one amino functionalized silicone is from about 0.1 to about 3 wt. %, or preferably about 0.3 to about 2.5 wt. %, or more preferably, about 0.4 to about 2 wt. %, or more preferably, about 0.5 to about 1.5 wt. %, or any suitable combination, sub-combination, range, or sub-range thereof by weight, based on the weight of the composition. One of ordinary skill in the art, however, will appreciate that other ranges are within the scope of the invention.

Thus, any one of the at least one amino functionalized silicone is present, by weight, based on the total weight of the composition, in an amount of from about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, to about 3 wt. %, including increments and ranges therein and there between.

Plant-Based Fatty Compounds

The at least one plant-based fatty compounds of the compositions of the present invention may be selected from plant-based oils, plant-based butters, plant-based triglycerides, or mixtures thereof.

Non-limiting examples of plant-based or vegetal oils include acai oil, almond oil, aloe vera oil, andiroba oil, annatto oil, avocado oil, babassu oil, borage oil, brazil nut oil, buriti oil, camelina oil, coffee oil, copaiba oil, emu oil, passion fruit oil, almond oil, castor oil, coconut oil, grapeseed oil, jojoba oil, macadamia nut oil, rose hip oil, ajwain oil, angelic root oil, anise oil, aragan oil, asafetida, balsam oil, basil oil, bay oil, bergamot oil, black pepper essential oil, buchu oil, birch oil, camphor, cannabis oil, caraway oil, cardamom seed oil, carrot seed oil, chamomile oil, calamus root oil, cinnamon oil, citronella oil, clary sage, clove leaf oil, coffee, coriander oil, costmary oil, cranberry seed oil, cubeb, cumin oil, cypress, cypriol, curry leaf, davana oil, dill oil, elecampane, eucalyptus oil, fennel seed oil, fenugreek oil, fir, frankincense oil, galangal, geranium oil, ginger oil, goldenrod, grapefruit oil, henna oil, helichrysum, horseradish oil, hyssop, Idaho tansy, jasmine oil, juniper berry oil, lavender oil, lemon oil, lemongrass, marjoram, melaleuca, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, perilla oil, pennyroyal oil, peppermint oil, petitgrain, pine oil, plum oil, ravensara, red cedar, roman chamomile, rose oil, rosehip oil, rosemary oil, rosewood oil, sandalwood oil, sassafras oil, savory oil, schisandra oil, spikenard, spruce, star anise oil, tangerine, tarragon oil, tea tree oil, thyme oil, tsuga oil, turmeric, valerian, vetiver oil, western red cedar, wintergreen, yarrow oil, ylang-ylang, and zedoary oil, sunflower oil, olive oil, marula oil, corn oil, argan oil, soybean oil, marrow oil, flax oil, sesame oil, hazelnut oil, apricot oil, arara oil, shea butter oil and rapeseed oil.

Suitable plant-based fatty compounds for use in the compositions of the present invention can also be selected from plant-based or vegetal butters such as shea butter (*Butyrospermum parkii*), Karite Nilotica butter (*Butyrospermum parkii*), galam butter, (*Butyrospermum parkii*), Borneo butter or fat or tengkawang tallow (*Shorea stenoptera*), shorea butter, illipe butter, madhuca butter or *Bassia madhuca longifolia* butter, mowrah butter (*Madhuca latifolia*), katiau butter (*Madhuca mottleyana*), phulwara butter (*M. butyracea*), mango butter (*Mangifera indica*), murumuru butter (*Astrocaryum murumuru*), kokum butter (*Garcinia indica*), ucuuba butter (*Virola sebifera*), tucuma butter, painya butter (Kpangnan) (*Pentadesma butyracea*), coffee butter (*Coffea arabica*), apricot butter (*Prunus armeniaca*), macadamia butter (*Macadamia ternifolia*), grapeseed butter (*Vitis vinifera*), avocado butter (*Persea gratissima*), olive butter (*Olea europaea*), sweet almond butter (*Prunus amygdalus dulcis*), cocoa butter (*Theobroma cacao*) and sunflower butter.

In a preferred embodiment, the suitable plant-based fatty compound of the present invention is selected from shea butter (*Butyrospermum parkii*).

The total amount of the plant-based fatty compounds in the composition may vary but is typically from of about 0.1 to about 10 wt %, about 0.1 to about 9 wt. %, or about 0.2 to about 8 wt. %, or about 0.3 to about 7 wt. %, or about 0.4 to about 7 wt. %, or about 0.4 to about 6.5 wt. %, or about 0.5 to about 6 wt. %, or 0.5 to about 5 wt. %, or about 0.1 to about 5 wt %, or about 0.5 to about 4.5 wt. %, or about 0.8 to about 4.2 wt. %, or about 1 to about 4 wt. %, or about 1.2 to about 4 wt. %, or about 1.2 to about 3.5 wt. %, or about 1.5 to about 3 wt %, or about 1 to about 3 wt. %, or about 1.5 to about 2.5 wt %, based on the total weight of the composition, including ranges and sub-ranges there between.

Thus, the plant-based fatty compounds is present, by weight, based on the total weight of the composition, in an amount from about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5 to about 5 wt. %, including increments and ranges therein and there between.

Fatty Alcohol

In accordance with the disclosure, compositions hereof include at least one fatty alcohol.

The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

The fatty alcohol(s) may be liquid or solid. In some instances, it is preferable that the hair cosmetic compositions include at least one solid fatty alcohol. The solid fatty alcohols that can be used include those that are solid at ambient temperature and at atmospheric pressure (25° C., 780 mmHg), and are insoluble in water, that is to say they have a water solubility of less than 1% by weight, preferably less than 0.5% by weight, at 25° C., 1 atm.

The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

In particular, it is possible to mention, alone or as a mixture: lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol).

Preferably, the solid fatty alcohol is chosen from cetyl alcohol, stearyl alcohol, behenyl alcohol and mixtures thereof such as cetylstearyl or cetearyl alcohol.

The liquid fatty alcohols, in particular those containing C10-C34, preferably have branched carbon chains and/or have one or more, preferably 1 to 3 double bonds. They are preferably branched and/or unsaturated (C=C double bond), and contain from 12 to 40 carbon atoms.

The liquid fatty alcohols may be represented by: R—OH, wherein R denotes a C12-C24 branched alkyl group or an alkenyl group (comprising at least one C12-C24 double bond C=C), R being optionally substituted by one or more hydroxy groups. Preferably, the liquid fatty alcohol is a branched saturated alcohol. Preferably, R does not contain a hydroxyl group. These include oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and mixtures thereof. Preferably, the liquid fatty alcohol is 2-octyl-1-dodecanol.

In some instances, the hair cosmetic compositions include one or more fatty alcohols selected from decyl alcohol, undecyl alcohol, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the hair cosmetic compositions preferably include cetearyl alcohol.

In accordance with the various embodiments, the amount of each of the at least one fatty alcohol is from about 1 to about 10 wt. %, or about 2 to about 9 wt. %, or about 3 to about 8 wt. %, or about 3.5 to about 7 wt. %, or about 4 to about 7 wt. %, or about 4.5 to about 6.5 wt. %, or about 5 to about 6 wt. %, or any suitable combination, sub-combination, range, or sub-range thereof by weight, based on the weight of the composition.

In certain preferred embodiments, the total amount of the at least one fatty alcohol is at least 3 wt. %, or at least 3.5 wt. %, or at least 4 wt. % or at least 4.5 wt. % or at least 5 wt. % or at least 5.5 wt. % or at least 6 wt. %, or is in an amount of from about 3 to about 10 wt. %, or about 3.5 to about 10 wt. %, or about 4 to about 9 wt. %, or about 4.5 to about 8.5 wt. %, or about 4.5 to about 8 wt. %, or about 5 to about 7.5 wt. %, or about 5.5 to about 7 wt. %, or about 5.5 to about 7 wt. %, or any suitable combination, sub-combination, range, or sub-range thereof by weight, based on the weight of the composition.

Thus, any one of the at least one fatty alcohol is present, by weight, based on the total weight of the composition, in an amount of from about 0.5, 0.6, 0.7, 0.8, 0.9, 1, 1.1, 1.2, 1.4, 1.5, 1.6, 1.7, 1.8, 1.9, 2, 2.1, 2.2, 2.3, 2.4, 2.5, 2.6, 2.7, 2.8, 2.9, to about 3 wt. %, including increments and ranges therein and there between.

Esters

The esters may be selected from fatty esters, cetyl esters, isopropyl esters, glyceryl (glycerol) esters, dialkyl esters, diesters with octanoic acid and propylene glycol (for example, mixture of the propylene glycol diesters of caprylic and capric acids, INCI: propylene glycol dicaprylate/dicaprate), or mixtures thereof.

Thus, the total amount of esters in the composition, may vary but is typically from about 0.01 to about 6 wt %, such as about 0.05 to about 5.5 wt. %, or about 0.05 to about 5 wt. %, or about 0.05 to about 4.5 wt. %, or about 0.1 to about 4 wt. %, or about 0.2 to about 3.5 wt. %, or about 0.3 to about 3 wt. %, or about 4 to about 2.5 wt. %, or about 0.5 to about 2 wt. %, or about 0.5 to about 1.5 wt. %, based on the total weight of the composition, including ranges and sub-ranges there between.

Additional Ingredients

The compositions of the present invention may further comprise additional/optional ingredients such as nonionic surfactants.

The nonionic surfactants may be selected from alkoxylated fatty alcohols such as oleth-3, oleth-10, oleth-20, trideceth-5, trideceth-6, trideceth-10, PPG-1 trideceth-6, laureth-12, steareth-20, and combinations thereof, Cosmetically Acceptable Solvent The cosmetically acceptable solvent may be chosen from water, organic solvents, or mixtures thereof.

In an embodiment, the cosmetically acceptable solvent in the compositions of the present invention comprises water.

In an embodiment, the cosmetically acceptable solvent in the compositions of the present invention comprises at least one organic solvent.

In an embodiment, the cosmetically acceptable solvent in the compositions of the present invention comprises water and at least one organic solvent.

Water

The amount of water in the hair cosmetic compositions may be at least 50 wt. %, or from about 50 to about 95 wt. %, about 50 to about 90 wt. %, about 60 to about 90 wt. %, about 70 to about 88 wt. %, about 75 to about 86 wt. %, based on the weight of the composition, including ranges and sub-ranges there between.

Organic Solvents

Non-limiting examples of organic solvents include, for example, alcohols (for example, $C_{1-15}$, $C_{1-10}$, or $C_{1-6}$ alcohols), organic solvents, polyols (polyhydric alcohols and glycols (e.g., glycerin, propylene glycol, butylene glycol, caprylyl glycol, etc.), and a mixture thereof.

Non-limiting examples of organic solvents include monoalcohols and polyols such as ethyl alcohol, isopropyl alcohol, propyl alcohol, benzyl alcohol, and phenylethyl alcohol, or glycerin or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of organic solvents include alkanediols such as 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monom-ethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In certain embodiments, the at least one organic solvent (non-silicone solvents) includes one or more of propylene glycol, glycerin, ethanol, isopropanol, caprylyl glycol, and benzyl alcohol.

The total amount organic solvent(s) in the hair cosmetic composition, if present, can vary but is typically about 0.01 to about 10 wt. %, based on the total weight of the hair cosmetic composition. In some cases, the total amount of water-soluble solvent(s) is about 0.05 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, about 0.5 to about 5 wt. %, about 0.5 to about 4 wt. %, or about 0.5 to about 3 wt. %, including all ranges and subranges there between, based on the total weight of the hair cosmetic composition.

In an embodiment, the cosmetically acceptable solvent in the compositions of the present invention comprises water and propylene glycol.

In an embodiment, the at least one organic solvent in the compositions of the present invention includes propylene glycol. When present, propylene glycol is in an amount of from about 0.1 to about 6 wt. %, about 0.1 to about 5 wt. %, about 0.5 to about 10 wt. %, about 0.5 to about 8 wt. %, about 0.5 to about 6 wt. %, about 0.5 to about 5 wt. %, about 0.5 to about 4 wt. %, or about 0.5 to about 3 wt. %, including all ranges and subranges there between, based on the total weight of the hair cosmetic composition.

In an embodiment, the cosmetically acceptable solvent in the compositions of the present invention comprises water and glycerin and/or other higher molecular weight glycol. When present, glycerin and/or other higher molecular weight glycol is in an amount of from about 0.05 to about 2 wt. %, about 0.05 to about 1.5 wt. %, about 0.1 to about 1 wt. %, about 0.1 to about 0.8 wt. %, about 0.1 to about 0.6 wt. %, about 0.1 to about 0.5 wt. %, about 0.1 to about 0.4 wt. %, or about 0.1 to about 0.3 wt. %, including all ranges and subranges there between, based on the total weight of the hair cosmetic composition.

In an embodiment, the cosmetically acceptable solvent in the compositions of the present invention comprises water, propylene glycol, and glycerin.

Other Components

In one or more embodiments, the hair cosmetic compositions described herein may contain one or more additional ingredients (additives and miscellaneous ingredients). Examples include, but are not limited to amphoteric surfactants, anionic surfactants, emulsifiers (such as sorbitan esters or polysorbates), thickeners (such as polysaccharide-based thickeners other than cationic guar gums), film formers, other polymers such as cationic polymers, amphoteric polymers, polyquaternium compounds such as polyquaternium-4, polyquaternium-6, polyquaternium-7, polyquaternium-10, polyquaternium-11, polyquaternium-22, polyquaternium-37, polyquaternium-53, polyquaternium-67, etc.), proteins, hydrolyzed proteins, amino acids, fragrance, pH adjusters, chelants, and preservatives.

In an embodiment, the compositions of the present disclosure are in the form of a leave-on product such as a styling/shaping product, leave-on product for curly hair (such as combing creams), anti-frizz hair product, or rinse-off or leave-on mask or treatment product.

In an embodiment, the compositions of the present disclosure are in the form of a rinse-off product such as a mask product.

In an embodiment, the compositions of the present disclosure are in the form of a leave-on product such as a styling/shaping product.

In an embodiment, the compositions of the present disclosure are in the form of a leave-on product such as a styling/shaping and conditioning product.

In an embodiment, the compositions of the present disclosure are in the form of a leave-on or a rinse-off styling conditioner.

In an embodiment, the compositions of the present disclosure are in the form of a cream.

In an embodiment, the compositions of the present disclosure are in the form of an emulsion such as an oil-in-water emulsion or a water-in-oil emulsion. In an embodiment, the emulsion is in the form of a cream.

In an embodiment, the compositions of the present disclosure are in the form of a gel cream.

Methods

Another aspect of the invention pertains to methods of using the hair cosmetic compositions described herein. The methods generally comprise applying any of the hair cosmetic compositions described to hair. The hair cosmetic compositions may be useful in a variety of settings, and either for chemically treated or untreated hair. Use on treated hair can include chemically relaxed/straightened hair or chemically dyed or bleached or lightened/highlighted hair. Use on hair may include as part of a shampoo, part of a conditioner or as a conditioner, as a pre-treatment, or after cleansing or conditioning or washing the hair as a leave-on treatment for styling/shaping the hair or caring for curly hair or as a leave-on or rinse-off mask treatment.

Methods of treating hair according to the disclosure may include applying a hair cosmetic composition of the instant disclosure to the hair (wet, damp, or dry hair), allowing the hair treatment to remain on the hair for a sufficient amount of time, and rinsing the hair cosmetic composition from the hair or allowing the hair treatment to be left on the hair as a leave-on product. The hair cosmetic composition may be applied to the hair before, during, or after other hair cosmetic compositions (e.g., a shampoo, a conditioner, a mask, a cream, a lotion, a gel, etc.).

Other methods of treating hair according to the disclosure involve a wash and go/braiding technique. Typically, the hair type on which this method is used is curly hair.

Other methods of treating hair according to the disclosure involve a twist out technique. Typically, the hair type on which this method is used is curly hair.

The hair cosmetic composition may be allowed to remain on the hair for a period of time, for example from about a few seconds (1, 3, 5, or 10 seconds) to about 10, 20, or 30 minutes, or longer such as up to about one hour or up to about two hours or up to about three hours or up to about four hours or up to about five hours or up to about six hours or up to about seven hours or up to about eight hours or up to about 12 hours or overnight.

The hair cosmetic compositions may be useful for treating chemically treated hair.

Described above is the individual application of a hair cosmetic composition or the combined or layered application of a hair cosmetic composition with another composition. In some cases, a hair cosmetic composition is individually applied to the hair and also combined or layered with another composition that is also applied to the hair.

Kits

The hair cosmetic compositions of the instant disclosure may be incorporated into a kit. For example, the kits may include at least one hair cosmetic composition according to the instant disclosure. The kits may also include one or more hair cosmetic compositions (according the instant disclosure), a shampoo and/or a conditioner and/or a mask and/or other hair treatment of styling product.

Implementation of the present disclosure is provided by way of the following examples. The examples serve to illustrate the technology without being limiting in nature.

EXAMPLES

The following Examples are intended to be non-restrictive and explanatory only. The ingredient amounts in the compositions/formulas described below are expressed in % by weight, based on the total weight of the composition.

Several formulas were produced having the ingredients as listed in the tables below. The balance of all formulas was water.

Example I: Compositions

TABLE 1

| | Formulation Examples | | |
|---|---|---|---|
| INGREDIENT TYPE | INGREDIENT INCI NAME | A invention | B comparative |
| CATIONIC VINYLPYRROLIDONE COPOLYMER | VP/DIMETHYLAMINOETHYL-METHACRYLATE COPOLYMER(1) | 0.8 | — |

TABLE 1-continued

| | Formulation Examples | | |
|---|---|---|---|
| INGREDIENT TYPE | INGREDIENT INCI NAME | A invention | B comparative |
| ACRYLATE-BASED POLYMER | ACRYLATES COPOLYMER(2) | 0.3 | — |
| CATIONIC GUAR GUM | GUAR HYDROXYPROPYLTRIMONIUM CHLORIDE | 0.30 | — |
| CATIONIC SURFACTANT | BEHENTRIMONIUM CHLORIDE | 0.5 | 0.8 |
| | CETRIMONIUM CHLORIDE | 0.02 | 0.02 |
| AMINO FUNCTIONALIZED SILICONE | AMODIMETHICONE(3) | 0.9 | 1.4 |
| PLANT-BASED FATTY COMPOUND | BUTYROSPERMUM PARKII (SHEA) BUTTER | 2.0 | — |
| | PLANT OILS | | 0.2 |
| FATTY ALCOHOL | CETEARYL ALCOHOL | 6.0 | 5.0 |
| ESTERS | CETYL ESTERS | 1.0 | — |
| ORGANIC SOLVENTS | PROPYLENE GLYCOL | 2.0 | |
| | ONE OR MORE OF GLYCERIN, CAPRYLYL GLYCOL, ISOPROPYL ALCOHOL | 0 to 0.5 | 0 to 0.5 |
| ADDITIVES OR MISCELLANEOUS INGREDIENTS | ONE OR MORE OF PRESERVATIVES, PH ADJUSTERS, CHELANTS, NONIONIC SURFACTANTS, COLORANTS, XYLOSE, SALT, FRAGRANCE, VITAMINS, PLANT EXTRACTS, PROTEINS/AMINO ACIDS/PROTEIN HYDROLYSATES | <5.0 (1.3-2) | <5.0 (1.3-2) |
| SOLVENT | WATER | QS 100 | QS 100 |

(1)commercially available under the tradename COPOLYMER 845-O from the company ISP (Ashland)

(2)commercially available under the tradename DAITOSOL 5000 AD from the company Daito Kasei Kogyo (3)commercially available under the tradenames XIAMETER 2-8299 or DOWSIL 2-8299 from the company Dow Corning/Dow Chemical or BELSIL ADM 4000 E from the company Wacker

TABLE 2

| | Formulation Examples | | | | |
|---|---|---|---|---|---|
| | | FORMULAS A (INVENTION) AND C TO E (COMPARATIVE) | | | |
| INGREDIENT TYPE | INGREDIENT INCI NAME | A invention | C | D | E |
| CATIONIC VINYLPYRROLIDONE COPOLYMER | VP/DIMETHYLAMINOETHYL-METHACRYLATE COPOLYMER(1) | 0.79 | — | 0.79 | — |
| ACRYLATE-BASED POLYMER | ACRYLATES COPOLYMER(2) | 0.25 | — | — | — |
| CATIONIC GUAR GUM | GUAR HYDROXYPROPYLTRIMONIUM CHLORIDE | 0.30 | 0.30 | 0.30 | 0.20 |
| CATIONIC SURFACTANT | BEHENTRIMONIUM CHLORIDE | 0.47 | 0.47 | 0.47 | 0.47 |
| | CETRIMONIUM CHLORIDE | 0.015 | 0.015 | 0.015 | — |
| AMINO FUNCTIONALIZED SILICONE | AMODIMETHICONE(3) | 0.86 | 0.86 | 0.86 | — |
| PLANT-BASED FATTY COMPOUND | BUTYROSPERMUM PARKII (SHEA) BUTTER | 2.0 | 1.0 | 1.0 | 1.0 |
| FATTY ALCOHOL | CETEARYL ALCOHOL | 6.0 | 5.0 | 5.- | 6.0 |
| ESTERS | CETYL ESTERS | 1.0 | 1.0 | 1.0 | 1.0 |
| ORGANIC SOLVENTS | PROPYLENE GLYCOL | 2.0 | 2.0 | 2.0 | — |
| | GLYCERIN | — | — | — | 2.0 |
| | ONE OR MORE OF CAPRYLYL GLYCOL, ISOPROPYL ALCOHOL | 0.11 | 0.11 | 0.11 | 0.11 |

TABLE 2-continued

Formulation Examples

| | | FORMULAS A (INVENTION) AND C TO E (COMPARATIVE) | | | |
|---|---|---|---|---|---|
| INGREDIENT TYPE | INGREDIENT INCI NAME | A invention | C | D | E |
| ADDITIVES OR MISCELLANEOUS INGREDIENTS | ONE OR MORE OF PRESERVATIVES, PH ADJUSTERS, CHELANTS, NONIONIC SURFACTANTS, COLORANTS, XYLOSE, SALT, FRAGRANCE, VITAMINS, PLANT EXTRACTS, PROTEINS/AMINO ACIDS/PROTEIN HYDROLYSATES | <5.0 (1.3-2) | <5.0 (1.3-2) | <5.0 (1.3-2) | <5.0 (1.3-2) |
| SOLVENT | WATER | QS 100 | QS 100 | QS 100 | QS 100 |

(1)commercially available under the tradename COPOLYMER 845-O from the company ISP (Ashland)
(2)commercially available under the tradename DAITOSOL 5000 AD from the company Daito Kasei Kogyo
(3)commercially available under the tradenames XIAMETER 2-8299 or DOWSIL 2-8299 from the company Dow Corning/Dow Chemical or BELSIL ADM 4000 E from the company Wacker Process of Making the Invention Composition:

The invention formula A was prepared according to the following general process:

1. Add 26% of water to a side kettle, start mixing, add cationic guar gum and mix until dispersed.
2. Add 28% of water to a main kettle, start heating to 70-75° C., add fatty alcohol, cationic surfactant(s), plant-based fatty compound(s), ester(s), and organic solvent(s), and mix until all melted and uniform.
3. Start cooling and add cationic vinylpyrrolidone copolymer, aminofucntionalized silicone, and homogenize.
4. Add side kettle phase to main kettle, add remaining water and homogenize.
5. Add preservatives, if any, and mix.
6. Cool and add acrylate-based polymer and homogenize.

When treated or contacted with the inventive formula A, it was observed that the film or coating formed on the hair fibers in a swatch was not crunchy, i.e., the film was not brittle and did not break easily. Moreover, the fibers remained coated and flexible even when the hair was subjected to bending, deformation, or compression. This indicated the resiliency of the hair and ability of the hair to maintain a desired shape or style even when subjected to deformation, Example II: Assessment of Test Formulations in Tables 1 and 2 when Applied onto Hair

TABLE 3

Observations

| Formulas | Cosmetic effect on hair swatches (wavy to moderately curly hair) and/or formulation texture |
|---|---|
| A (invention) vs B (without cationic vinylpyrrolidone copolymer and acrylate-based polymer, with 0 to 0.5 wt. % glycerin) | Hair treated with Inventive Formula A demonstrated curl hold and definition for a longer period of time (e.g., overnight after sleeping) compared to hair treated with Comparative Formula B. Hair treated with Inventive Formula A demonstrated better styling/shaping and curl definition compared to hair treated with Comparative Formulas C, D, and E. |
| C (without cationic vinylpyrrolidone copolymer and acrylate-based polymer, with propylene glycol) | Comparative Formula C provided a light weight feel on hair compared to Comparative Formula E; Comparative Formula C demonstrated much less curl hold and definition compared to Inventive Formula A. |
| D (without acrylate-based polymer, with propylene glycol) | Comparative Formula D provided curl definition and had a higher viscosity compared to Comparative Formulas E and C; however, Comparative Formula D demonstrated less curl hold and definition for a longer period of time (e.g., overnight after sleeping) compared to hair treated with Inventive Formula A. |
| E (without cationic vinylpyrrolidone copolymer and acrylate-based polymer, with glycerin) | Comparative formula E imparted a heavier coating on the hair compared to Comparative Formulas A, C, and D. |

Example III Performance Testing on Hair

Test Protocols:

A. Protocol a—Swatch Testing:

Test hair swatches were first treated with a rinse-out shampoo followed by a rinse-out conditioner. The hair swatches were towel-dried and then treated with the inventive formula or a comparative formula. To mimic overnight use (tossing and turning when asleep), the swatches were turned and rubbed against each other and a towel for ten times. The swatches were then left in a humidity chamber for 12 hours at 25° C. and 80% humidity ("overnight" use test).

B. Protocol B—In Vivo/Consumer Testing:

Human female volunteers were instructed to follow their regular hair routine at night and then apply the invention/test formula to damp or towel-dried hair. The women volunteers who were selected typically wash their hair at night. Additional criteria of test subjects were of similar hair length, hair texture of normal to coarse, curl type of slightly curly (or wavy) to moderately curly.

After their regular hair routine at night, the volunteers dispensed the desired amount of the invention/test formula (starting with a dime size and applying more as needed) in their hands, rubbed their hands together, and evenly applied the formula to damp hair. They then styled their hair as they normally would before going to sleep.

Example IIIA

In Vitro Testing of the Invention on Swatches

The test formulas—invention formula and comparative formulas—were tested on hair swatches. The comparative formulas either did not contain both the cationic vinylpyrrolidone polymer (e.g., VP/dimethylaminoethylmethacrylate copolymer) and the acrylate-based polymer (e.g., acrylates copolymer) of the invention or contained different amounts of the acrylate-based polymer (0.25 to 0.75 wt. %, active weight). The hair swatches were treated as described in protocol A above and subjected to the "overnight use" step.

After the overnight use step, the swatches were evaluated. The table below describes the evaluation results at two time points: (T1) pre-breaking and (T2) post-breaking. The term "breaking" as used herein refers to the action of running the fingers at least two times through the hair.

TABLE 4

Swatch Evaluation at Two Time Points

| Formula | Pre Breaking-Ambient Conditions | Post Breaking-Ambient Conditions |
|---|---|---|
| Formula A1 (No polymers) | rigid, low curl pattern, closed ends | regular curls, open ends |
| Formula A1-a: Formula A1 + 0.25% acrylates copolymer (2) | rigid, low curl pattern, closed ends | closed ends, more regular curls |
| Formula A1-b: Formula A1 + 0.5% acrylates copolymer (2) | rigid, elongated, and irregular | irregular curls, closed ends |
| Formula A1-c: Formula A1 + 0.75% acrylates copolymer (2) | rigid but less stiff than others, most elongated | irregular elongated curls, closed ends |
| Formula A (Invention) | rigid, more regular curls, closed ends | regular, even curls, closed ends, |

(2) commercially available under the tradename DAITOSOL 5000 AD from the company Daito Kasei Kogyo The observations in Table 4 indicate that at time point T1, the swatches treated with the comparative formulas (without polymers and with only acrylates copolymer) exhibited low or elongated curl patterns while the swatch treated with the invention formula A exhibited similar or better curl patterns but with more closed ends which were desirable (ends of the hair were more sealed and not opening up). At this time point, results between the comparative formulas and the invention were comparable and may be attributed to the wet/damp condition of the hair.

At the time point T2, after the "overnight" period, the swatches treated with the invention formula exhibited significantly better curl definition, regularity of curls, and a more sleek look compared to the swatches treated with the comparative formulas and also compared to the swatches treated with the invention and comparative formulas at time point T1. At the same time, at T2, the swatches treated with the invention formula exhibited a significantly better closed end look compared to the swatches treated with the comparative formulas. The swatch images in FIG. 1 The Figure show the results at T2 (post-breaking).

The results above indicate that while using a formula with only the acrylates copolymer can help maintain and/or provide curl patterns to hair immediately after treating wet/damp hair and after a period of time (e.g., overnight), using a formula that had both cationic vinylpyrrolidone and acrylate-based polymers produced the best curl patterns and closed end look, even after the "overnight" period.

Example IIIB

In Vivo Testing of the Invention

The invention composition was tested by women volunteers, at least 18 years of age, having curly hair (medium curly or moderately curly hair) for day time and night time application on wet/damp hair before styling their hair.

Overall, the women observed the following:

The style endured the evening and sleep routines and styling is easier in the morning (simplifies the routine).

Over a 2 week period, the hair style was consistent, day to day.

The composition was easy to apply, dose, and dispense and distributed evenly on hair.

With respect to styling attributes, the hair quickly takes the style in the morning, does not require too much effort to achieve the desired end-look. The hair style can be controlled. Hair was not messy in the morning.

With respect to curls, the hair demonstrated curl shape and definition even the next day. The hair was not greasy and did not become flat.

The hair did not look or feel dry, easy to detangle during application and the next day, and felt smooth and soft to the touch.

No product transfer was observed; the product dried quickly and did not wet/stain the pillow.

Example IIIC

In Viva Testing—Invention Composition Versus Comparative Formula G

TABLE 5

| | Comparative Formulation | |
|---|---|---|
| INGREDIENT TYPE | INGREDIENT INCI NAME | Comparative Formula G |
| CATIONIC VINYLPYRROLIDONE COPOLYMER | VP/DIMETHYLAMINOETHYL-METHACRYLATE COPOLYMER(1) | 0.6 |
| CATIONIC SURFACTANT | BEHENTRIMONIUM CHLORIDE | 0.8 |
| AMINO FUNCTIONALIZED SILICONE | AMODIMETHICONE | 0.8 |
| PLANT-BASED OILS | PLANT OILS | 4.0 to 6.0 |
| FATTY ALCOHOL | CETEARYL ALCOHOL | 2.0 |
| ESTERS | ESTERS | 3.0 |
| STARCH | STARCH DERIVATIVE | 1.4 |
| CATIONIC POLYMER | CATIONIC POLYMER | 1.5 |
| ORGANIC SOLVENTS | ONE OR MORE OF GLYCERIN, CAPRYLYL GLYCOL, ISOPROPYL ALCOHOL | 0.7 |
| ADDITIVES OR MISCELLANEOUS INGREDIENTS | ONE OR MORE OF PRESERVATIVES, PH ADJUSTERS, CHELANTS, COLORANTS, NONIONIC SURFACTANTS, XYLOSE, SALT, FRAGRANCE, VITAMINS, PLANT EXTRACTS, PROTEINS/AMINO ACIDS/PROTEIN HYDROLYSATES | <5.0 (1.3-2) |
| SOLVENT | WATER | QS 100 |

Test A:

The Inventive Formula A and Comparative Formula G were tested in a half-head/blind and randomized screening study by women volunteers, at least 18 years of age, having curly hair (medium or moderately curly hair). The hair of each volunteer was first washed with a conventional shampoo and conventional conditioner. A test composition was then applied to the hair on the designated side. Assessments were made during application, after drying the hair, and after 24 hours, i.e., the volunteers slept overnight with the test composition on the hair.

Generally, it was observed during the treatment of the hair, both test formulas were easy to apply and distributed well along the hair fibers. The comparative formula showed some drag along the fibers. After drying and 24 hours, more than half of the volunteers observed better curl definition and/or shaping control as well as discipline and/or frizz control on the hair treated with the Inventive Formula A.

Test B:

Inventive Formula A and Comparative Formula G were tested in a 2 cell monadic test by women volunteers, at least 18 years of age, having curly hair (medium or moderately curly hair). The volunteers applied the test formulas onto hair (day, morning time and/or night time application on wet/damp hair) after their usual hair care/hair washing routines before styling their hair. The test formulas were applied to damp hair from tips to roots.

TABLE 7

| | Comments and observations by volunteers | |
|---|---|---|
| Time Period | Inventive Formula A | Comparative Formula B |
| Morning | Defined curls, good frizz control<br>Soft/hydrated hair feel (not crunchy)<br>Long lasting definition<br>Amount of styling time as compared to usual routine is acceptable | Defined curls, good frizz control<br>Soft/hydrated hair feel (not crunchy)<br>Long lasting definition<br>Required more Amount of styling time as compared to usual routine |
| Overnight | Defined curls, good frizz control (more than half of volunteers)<br>Soft/hydrated hair feel (not crunchy) (more than half of volunteers)<br>Long lasting definition (more than half of volunteers)<br>Easier, faster styling time the next morning<br>Works best on damp hair | Curls were more elongated, less defined, less frizz control, hair had a more greasy feel (more than half of volunteers)<br><br><br>Used more effort to fix hair; sometimes had to completely re-wash and re-style<br>Works best on damp hair |

The results in Table 6 above show that the inventors surprisingly discovered a combination of ingredients that resulted in a composition that provided good styling and shaping hold, including curl definition that is long lasting, good frizz control, soft feel and hydrated feel, and other cosmetic attributes to hair even when the hair was treated the night before with the invention formula and it was slept on overnight. The morning after treating the hair, many of the volunteers found that it was easier, faster to style the hair, thereby leading to a simplification of the morning routine. These results demonstrate that compared to Comparative Formula G, the invention delivered night caring and styling benefits, including long lasting curl definition and long lasting frizz control to hair.

In summary, the examples above show that the inventors surprisingly discovered a combination of ingredients that resulted in compositions that when applied to hair provided night caring and styling benefits, long lasting styling and shaping hold, including curl definition, good frizz control, no product build-up, detangling, and other cosmetic attributes to hair even when the hair was slept on for several hours (whether at night or during the day).

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counterion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

The term "lasting" or "long lasting" or "durable" as used herein means that the cosmetic attribute or effect was observed up to about 30 minutes or up to about one hour or up to about two hours, or up to about three hours or up to about four hours or up to about five hours or up to about six hours or up to about seven hours or up to about eight hours or up to about 12 hours or after an overnight period from the time the composition of the present disclosure was applied to hair on the head of a person and the hair was subjected to changes in the hair shape or style or configuration, and/or to disturbance of the hair fibers and/or to movement of the hair fibers as a result of sleeping or lying down and resting the head on a bed or other surface or the back part of a seat and/or as a result of wearing a head cap or cover for at least 30 minutes up to several hours or overnight.

Some of the various categories of components identified for the hair-treatment compositions may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty compound component and an emulsifier component, a single fatty acid can serve as only a fatty compound or a surfactant/emulsifier (a single fatty acid does not serve as both the fatty compound and the surfactant/emulsifier).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

Other than in the operating examples, or where otherwise indicated, all numbers expressing quantities of ingredients and/or reaction conditions are understood to be modified by "about," whether or not expressly stated. Additionally, all numbers are intended to represent exact figures as additional embodiments, whether or not modified by "about." For example, "an amount of about 1%" includes an amount of exactly 1%. As a further example, "an amount of 1%" includes an amount of about 1%. The term "about" is generally understood to encompass a range of +/−10% from the stated number, and is intended to cover amounts of +/−1%, 2%, 3%, 4%, 5%, 6%, 7%, 8%, 9%, and 10%.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 2% by weight of a specific material added to a composition, based on the total weight of the compositions (provided that an amount of less than 2% by weight does not materially affect the basic and novel characteristics of the claimed invention. Similarly, the compositions may include less than 2 wt %, less than 1.5 wt %, less than 1 wt %, less than 0.5 wt %, less than 0.3 wt %, less than 0.1 wt %, less than 0.05 wt %, or less than 0.01 wt %, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure.

The term "substantially free" or "essentially free" as used herein may also mean that the specific material is not added to the composition but may still be present in a raw material that is included in the composition.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A hair cosmetic composition comprising:
   (a) about 0.4 to about of about 1 wt. % of VP/dimethylaminoethylmethacrylate copolymer;
   (b) about 0.1 to about 1 wt. % of acrylates copolymer;
   (c) about 0.1 to about 1 wt. % of at least one cationic guar polymer selected from guar hydroxypropyltrimonium chloride, hydroxypropyl guar hydroxypropyl trimonium chloride, or a mixture thereof;
   (d) about 0.2 to about 2 wt. % of at least one cationic or cationizable surfactant;
   (e) about 0.4 to about 2 wt. % of amodimethicone;
   (f) about 2 to about 6 wt. % of at least one plant oil, at least one plant butter, at least one plant triglyceride, or mixtures thereof;
   (g) about 4 to about 7 wt. % of at least one fatty alcohol;
   (h) about 0.1 to about 4 wt. % of at least one fatty ester; and
   (i) about 60 to about 90 wt. % of water;
      wherein the hair cosmetic composition is free of colorants and does not alter color of hair when applied to the hair, and all percentages by weight are based on a total weight of the hair cosmetic composition.

2. The hair cosmetic composition of claim 1, wherein (g) is in an amount greater than (h).

3. The hair cosmetic composition of claim 1, wherein the hair cosmetic composition is an oil-in-water emulsion.

4. The hair cosmetic composition of claim 1, wherein the at least one cationic guar polymer is guar hydroxypropyltrimonium chloride.

5. The hair cosmetic composition of claim 1, wherein the at least one cationic or cationizable surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyl dimethylamine, behenamidopropyl dimethylamine, behenamidopropyl diethylamine, behenamidoethyl diethylamine behenamidoethyl dimethylamine, arachidamidopropyl dimethylamine, arachidamidopropyl diethylamine, arachidamidoethyidiethylamine arachidamidoethyl diethylamine, arachidamidoethyl dimethylamine, brassicamidopropyl dimethylamine, lauramidopropyl dimethylamine, myristamidopropyl dimethylamine, dilinoleamidopropyl dimethylamine, palmitamidopropyl dimethylamine, or mixtures thereof.

6. The hair cosmetic composition of claim 1 comprising at least one plant butter and at least one plant oil.

7. The hair cosmetic composition of claim 6, wherein the at least one plant butter is shea butter.

8. The hair cosmetic composition of claim 7, wherein the at least one fatty alcohol is selected from cetyl alcohol, stearyl alcohol, cetearyl alcohol, behenyl alcohol, lauryl alcohol, myristic or myristyl alcohol, arachidyl alcohol, lignoceryl alcohol, ceryl alcohol, montanyl alcohol, myricylic alcohol, decyl alcohol, undecyl alcohol, or mixtures thereof.

9. The hair cosmetic composition of claim 7, wherein the at least one fatty ester is selected from cetyl esters, isopropyl esters, glyceryl esters, dialkyl esters, diesters with octanoic acid and propylene glycol, or mixtures thereof.

10. The hair cosmetic composition of claim 9 consisting of:
    (a) about 0.4 to about of about 1 wt. % of VP/dimethylaminoethylmethacrylate copolymer;
    (b) about 0.1 to about 1 wt. % of acrylates copolymer;
    (c) about 0.1 to about 1 wt. % of guar hydroxypropyltrimonium chloride;
    (d) about 0.2 to about 2 wt. % of at least one cationic or cationizable surfactant;
    (e) about 0.4 to about 2 wt. % of amodimethicone;
    (f) about 2 to about 6 wt. % of at least one plant oil and at least one plant butter;
    (g) about 4 to about 7 wt. % of at least one fatty alcohol;
    (h) about 0.1 to about 4 wt. % of at least one fatty ester;
    wherein (g) is in an amount greater than (h); and
    (i) about 60 to about 90 wt. % of water; and
    (j) less than 5 wt. % of one or more preservatives, pH adjusters, chelants, nonionic surfactants, xylose, salt, fragrances, vitamins, proteins, protein hydrolysates, amino acids, or mixtures thereof;
       wherein all percentages by weight are based on a total weight of the hair cosmetic composition.

11. A hair cosmetic composition comprising:
    (a) about 0.4 to about of about 1 wt. % of VP/dimethylaminoethylmethacrylate copolymer;
    (b) about 0.1 to about 1 wt. % of acrylates copolymer;
    (c) about 0.1 to about 1 wt. % of guar hydroxypropyltrimonium chloride;
    (d) about 0.2 to about 2 wt. % of at least one cationic or cationizable surfactant;
    (e) about 0.4 to about 2 wt. % of amodimethicone;

(f) about 2 to about 6 wt. % of at least one plant oil and at least one plant butter;
(g) about 4 to about 7 wt. % of at least one fatty alcohol;
(h) about 0.1 to about 4 wt. % of at least one fatty ester; wherein (g) is in an amount greater than (h); and
(i) about 60 to about 90 wt. % of water;
wherein the hair cosmetic composition is free of colorants and does not alter color of hair when applied to the hair, and all percentages by weight are based on a total weight of the hair cosmetic composition.

12. A hair cosmetic composition consisting of:
(a) at least one cationic vinylpyrrolidone copolymer;
(b) at least one acrylate containing polymer;
(c) at least one cationic guar polymer;
(d) at least one cationic or cationizable surfactant;
(e) at least one amino functionalized silicone;
(f) at least one fatty compound of plant origin;
(g) at least one fatty alcohol;
(h) at least one fatty ester; and
(i) a cosmetically acceptable solvent comprising water and optionally at least one organic solvent; and
(j) less than 5 wt. % of one or more preservatives, pH adjusters, chelants, nonionic surfactants, xylose, salt, fragrances, vitamins, plant extracts, proteins, protein hydrolysates, amino acids, or mixtures thereof;
wherein all percentages by weight are based on a total weight of the hair cosmetic composition.

13. A method of treating hair, the method comprising applying onto hair, the hair cosmetic composition of claim 1.

14. A method of treating hair, the method comprising applying onto hair, the hair cosmetic composition of claim 11.

15. A method of treating hair, the method comprising applying onto hair, the hair cosmetic composition of claim 12.

* * * * *